United States Patent
Furrer et al.

(10) Patent No.: US 8,435,270 B2
(45) Date of Patent: May 7, 2013

(54) ORTHOGNATHIC IMPLANT AND METHODS OF USE

(75) Inventors: Andre Furrer, Oberdorf (CH); Timo Zillig, Oberoorf (CH); Frank Wilde, Ulm (DE)

(73) Assignee: Synthes USA, LLC, West Chester, PA (US)

( * ) Notice: Subject to any disclaimer, the term of this patent is extended or adjusted under 35 U.S.C. 154(b) by 0 days.

(21) Appl. No.: 13/078,250

(22) Filed: Apr. 1, 2011

(65) Prior Publication Data

US 2012/0029574 A1 Feb. 2, 2012

Related U.S. Application Data

(63) Continuation-in-part of application No. 12/770,088, filed on Apr. 29, 2010.

(51) Int. Cl.
*A61B 17/80* (2006.01)
*G06F 17/00* (2006.01)

(52) U.S. Cl.
USPC .......................................... 606/280; 606/903

(58) Field of Classification Search ............ 606/280, 606/281, 283, 284, 285, 903; 700/98; 29/407.1
See application file for complete search history.

(56) References Cited

U.S. PATENT DOCUMENTS

| | | |
|---|---|---|
| 4,484,570 A | 11/1984 | Sutter et al. |
| 4,575,805 A | 3/1986 | Moermann et al. |
| 4,966,599 A | 10/1990 | Pollock |
| 4,976,737 A | 12/1990 | Leake |
| 5,052,930 A | 10/1991 | Lodde et al. |
| 5,306,150 A | 4/1994 | Gittleman |
| 5,364,396 A | 11/1994 | Robinson et al. |
| 5,373,860 A | 12/1994 | Catone |
| 5,452,407 A | 9/1995 | Crook |
| 5,622,493 A | 4/1997 | Razdolsky et al. |
| 5,690,631 A | 11/1997 | Duncan |
| 5,769,637 A | 6/1998 | Morgan |
| 5,836,948 A | 11/1998 | Zucherman |
| 5,885,283 A | 3/1999 | Gittleman |
| 5,895,387 A | 4/1999 | Guerrero et al. |
| 6,221,075 B1 | 4/2001 | Tormala |
| 6,254,639 B1 | 7/2001 | Peckitt |

(Continued)

FOREIGN PATENT DOCUMENTS

| | | |
|---|---|---|
| EP | 0 290 138 | 11/1988 |
| EP | 0 566 255 | 10/1993 |

(Continued)

OTHER PUBLICATIONS

U.S. Appl. No. 12/770,088, filed Apr. 29, 2010, Andre Furrer.

(Continued)

*Primary Examiner* — Kevin T Truong
*Assistant Examiner* — Christian Sevilla
(74) *Attorney, Agent, or Firm* — Woodcock Washburn LLP

(57) ABSTRACT

An implant for use in orthognathic surgery of a mandible may include a longitudinal plate member and a plurality of pre-configured guides coupled to the plate member. The longitudinal plate member is pre-bent to correspond to the post-operative shape of the mandible; and the guides are pre-configured to align the plate member with the mandible when the implant is positioned against the mandible after the mandible has been separated.

8 Claims, 19 Drawing Sheets

U.S. PATENT DOCUMENTS

| | | | |
|---|---|---|---|
| 6,712,851 B1 | 3/2004 | Lemperle et al. | |
| 6,863,694 B1 | 3/2005 | Boyce et al. | |
| 6,932,842 B1 | 8/2005 | Litschko et al. | |
| 6,972,020 B1 | 12/2005 | Grayson et al. | |
| 7,172,422 B1 | 2/2007 | Essiger | |
| 2002/0062127 A1 | 5/2002 | Schumacher et al. | |
| 2002/0116002 A1 | 8/2002 | Sellers | |
| 2003/0105463 A1 | 6/2003 | Wolgen | |
| 2003/0139748 A1 | 7/2003 | Koseki | |
| 2004/0138591 A1 | 7/2004 | Iseki et al. | |
| 2004/0166469 A1 | 8/2004 | Tremont | |
| 2005/0039759 A1 | 2/2005 | Mauro | |
| 2005/0059864 A1 | 3/2005 | Fromovich et al. | |
| 2005/0182408 A1 | 8/2005 | Pfefferle et al. | |
| 2005/0192675 A1 | 9/2005 | Robinson | |
| 2005/0256526 A1 | 11/2005 | Johnston | |
| 2006/0116682 A1 | 6/2006 | Longo | |
| 2006/0235408 A1* | 10/2006 | Wang et al. | 606/69 |
| 2007/0043370 A1 | 2/2007 | Ueda et al. | |
| 2007/0118243 A1* | 5/2007 | Schroeder et al. | 700/118 |
| 2008/0081315 A1 | 4/2008 | Kim et al. | |
| 2008/0195240 A1 | 8/2008 | Martin et al. | |
| 2009/0131944 A1 | 5/2009 | Noon et al. | |
| 2011/0301609 A1 | 12/2011 | Longepied | |

FOREIGN PATENT DOCUMENTS

| | | |
|---|---|---|
| EP | 0 748 616 | 12/1996 |
| EP | 0 890 345 | 1/1999 |
| EP | 1 088 520 | 4/2001 |
| EP | 1 468 656 | 10/2004 |
| EP | 1 502 556 | 2/2005 |
| EP | 2 030 596 | 3/2009 |
| EP | 2 179 701 | 4/2010 |
| JP | 09215699 | 8/1997 |
| JP | 10043203 | 2/1998 |
| JP | 2005028046 | 2/2005 |
| WO | WO 91/14404 | 10/1991 |
| WO | WO 97/20512 | 6/1997 |
| WO | WO 99/44529 | 9/1999 |
| WO | WO 01/34044 | 5/2001 |
| WO | WO 01/78612 | 10/2001 |
| WO | WO 02/28298 | 4/2002 |
| WO | WO 2005/117760 | 12/2005 |
| WO | WO 2006/020245 | 2/2006 |
| WO | WO 2007/142743 | 12/2007 |

OTHER PUBLICATIONS

International Patent Application No. PCT/US2010/032908: International Search Report dated Nov. 29, 2010, 7 pages.

International Patent Application No. PCT/US2011/030885: International Search Report dated Nov. 29, 2010, 7 pages.

* cited by examiner

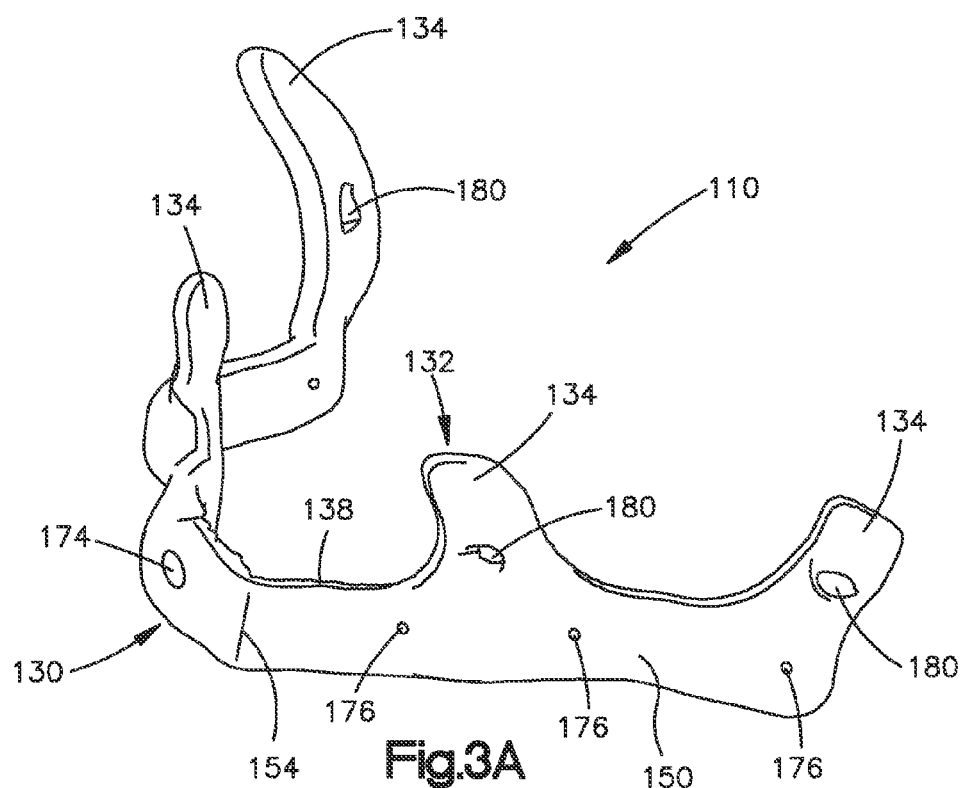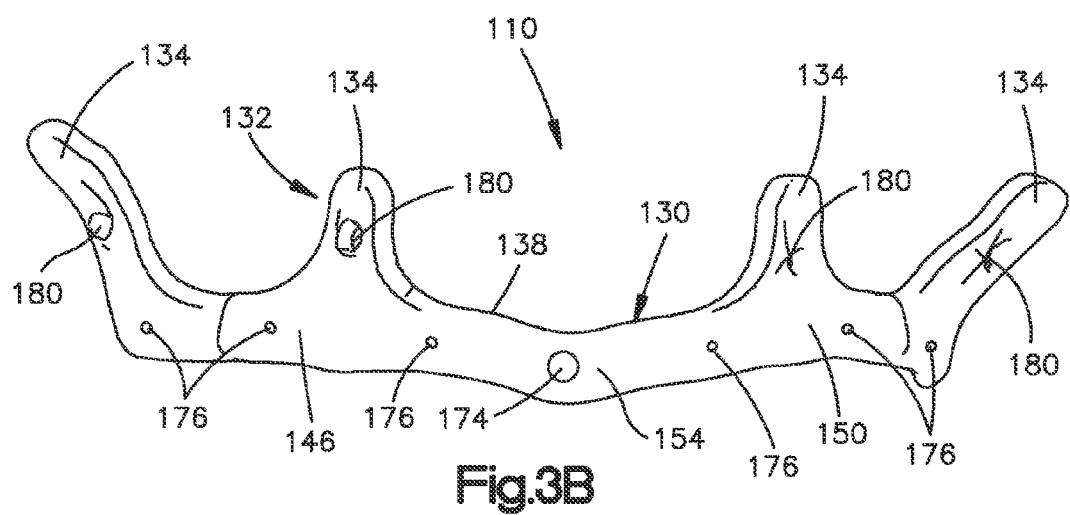

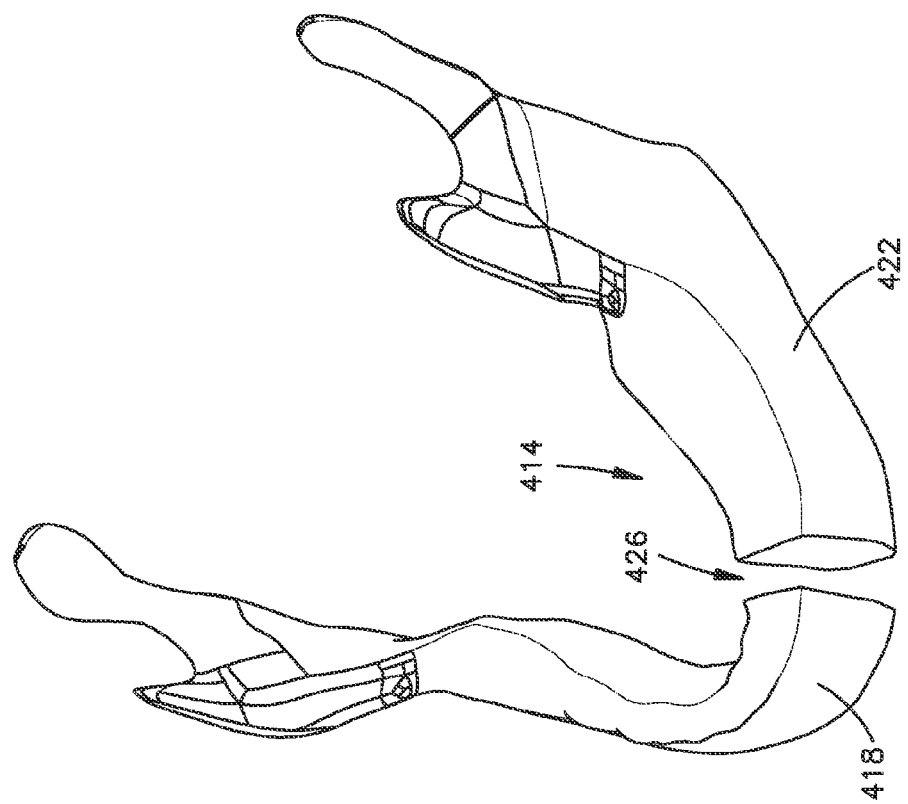
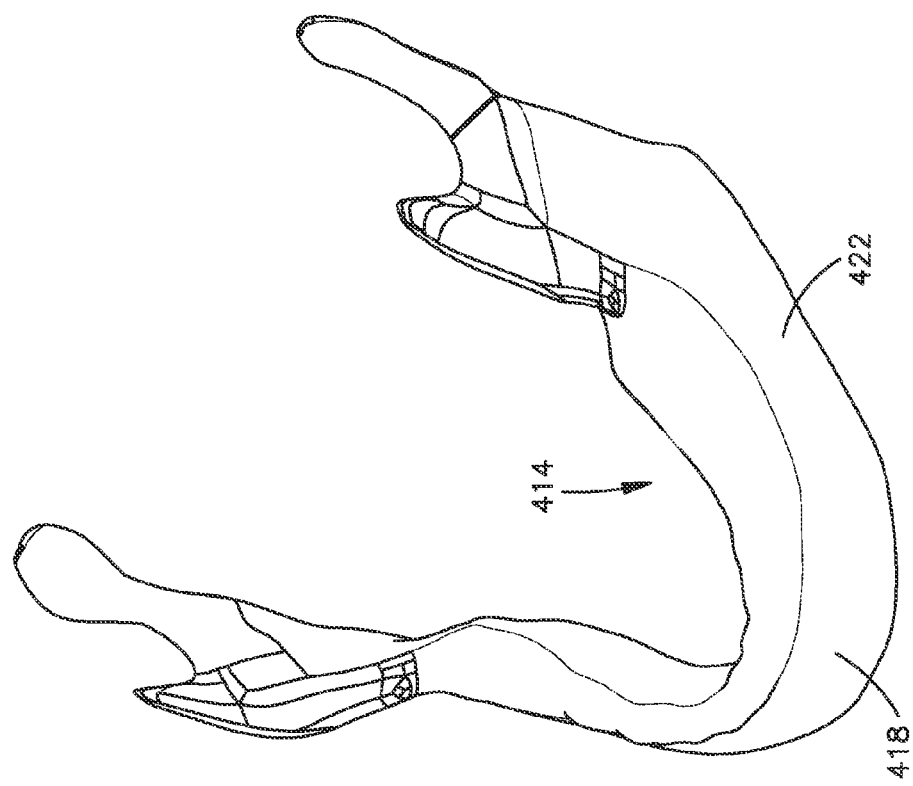

ORTHOGNATHIC IMPLANT AND METHODS OF USE

CROSS REFERENCE TO RELATED APPLICATIONS

This application is a continuation-in-part of U.S. patent application Ser. No. 12/770,088 filed Apr. 29, 2010, the disclosure of which is hereby incorporated by reference as if set forth in its entirety herein.

BACKGROUND

Orthognathic surgery is generally performed to correct conditions of the jaw (i.e. the mandible), maxilla, and face related to structure, growth, sleep apnea, TMJ disorders or to correct orthodontic problems. For example, an individual who has a significantly receded upper jaw or an open bite might benefit from a maxillary osteotomy. In such a procedure, a surgeon makes cuts below both eye sockets to separate a segmented part of the maxilla from an intact portion of the maxilla. The entire segmented part, including the roof of the mouth and all upper teeth, can move as a single unit. The segmented part is then moved until the upper and bottom teeth fit together properly. Once the teeth are realigned, tiny screws and plates are used to fix the segmented part of the maxilla in its new position until natural bone healing takes place.

Some orthognathic surgeries affix multiple plates to the maxilla to hold the cut segmented part of the maxilla relative to the second intact part. As one could imagine, the adaptation and use of multiple plates make the procedure unnecessarily long and complicated.

Similarly, an individual may require a mandible reconstruction due to trauma or a tumor. To remove the tumor, the surgeon may cut the mandible on either side of the tumor thereby separating the tumor from the mandible. Once the tumor is removed, the mandible is separated into a first part and a second part. If needed, the first part and/or the second part may be repositioned and tiny screws and plates are used to fix the first part and the second part together until natural bone healing takes place.

Other plating systems for orthognathic surgeries involving the maxilla and the mandible require multiple disciplines such as surgeons, dentists, orthodontists, etc to complete the procedure. As a result there often times are misunderstandings between the disciplines. These and other disadvantages are attributed to such plating systems used in orthognathic surgeries.

Therefore, it may be desired to achieve a better and more accurate way of planning and performing orthognathic surgery.

SUMMARY

The disclosure generally relates to an improvement in implants used in orthognathic surgery, and in particular, patient specific plates for use in orthognathic surgery. However, the disclosed implants are not limited to this specific application.

In one embodiment, an implant is configured to fix at least a first mandibular bone part relative to a second mandibular bone part that is separated from the first mandibular bone part by a bone gap. The bone implant may include a plate member and at least one guide coupled to the plate member. The plate member may include a pre-operatively bent body having a shape corresponding to a post-operative shape of a mandible when aligned with the mandible. The plate member defining at least one fixation aperture that extends through the pre-operatively bent body and is configured to receive a bone fixation element so as to secure the plate member to the mandible. The at least one guide may be pre-operatively configured to align the plate member with the mandible when the implant is positioned against the mandible after the mandible has been separated so as to define the bone gap.

A method of customizing a pre-configured implant configured to fix at least a first mandibular bone part relative to a second mandibular bone part that is separated from the first mandibular bone part by a bone gap. To customize the implant a pre-operative 3-D model of a patient's mandible is first obtained in a computer, whereby a first part of the mandible and a second part of the mandible define a first relative position. The pre-operative 3-D model of the mandible is the manipulated into a planned post-operative shape whereby the first part of the mandible and the second part of the mandible define a second relative position. Once in the desired position a bone fixation implant is custom constructed to match the planned post-operative shape of the mandible. The implant may include a plate member pre-bent to attach to the first part and the second part of the mandible, and at least one guide coupled to the plate member. The guide may be pre-configured so as to align the plate member with the mandible when the implant is positioned against the mandible after the mandible has been separated so as to define the bone gap.

BRIEF DESCRIPTION OF THE DRAWINGS

The foregoing summary, as well as the following detailed description of example embodiments, are better understood when read in conjunction with the appended diagrammatic drawings. For the purpose of illustrating the invention, the drawings show embodiments that are presently preferred. The invention is not limited, however, to the specific instrumentalities disclosed in the drawings.

FIG. 3A is a perspective view of an osteotomy guiding implant constructed in accordance with one embodiment;

FIG. 3B is a front elevation view of the osteotomy guiding implant shown in FIG. 3A;

FIG. 5A is a front elevation view of a skull, including a maxilla bone that is to be operated on;

FIG. 9A is a perspective view showing the pre-operative shape of a mandible;

FIG. 9B is a perspective view of the mandible shown in FIG. 9A, after the mandible has been segmented into a first part and a second part;

DETAILED DESCRIPTION OF ILLUSTRATIVE EMBODIMENTS

Figure 1:
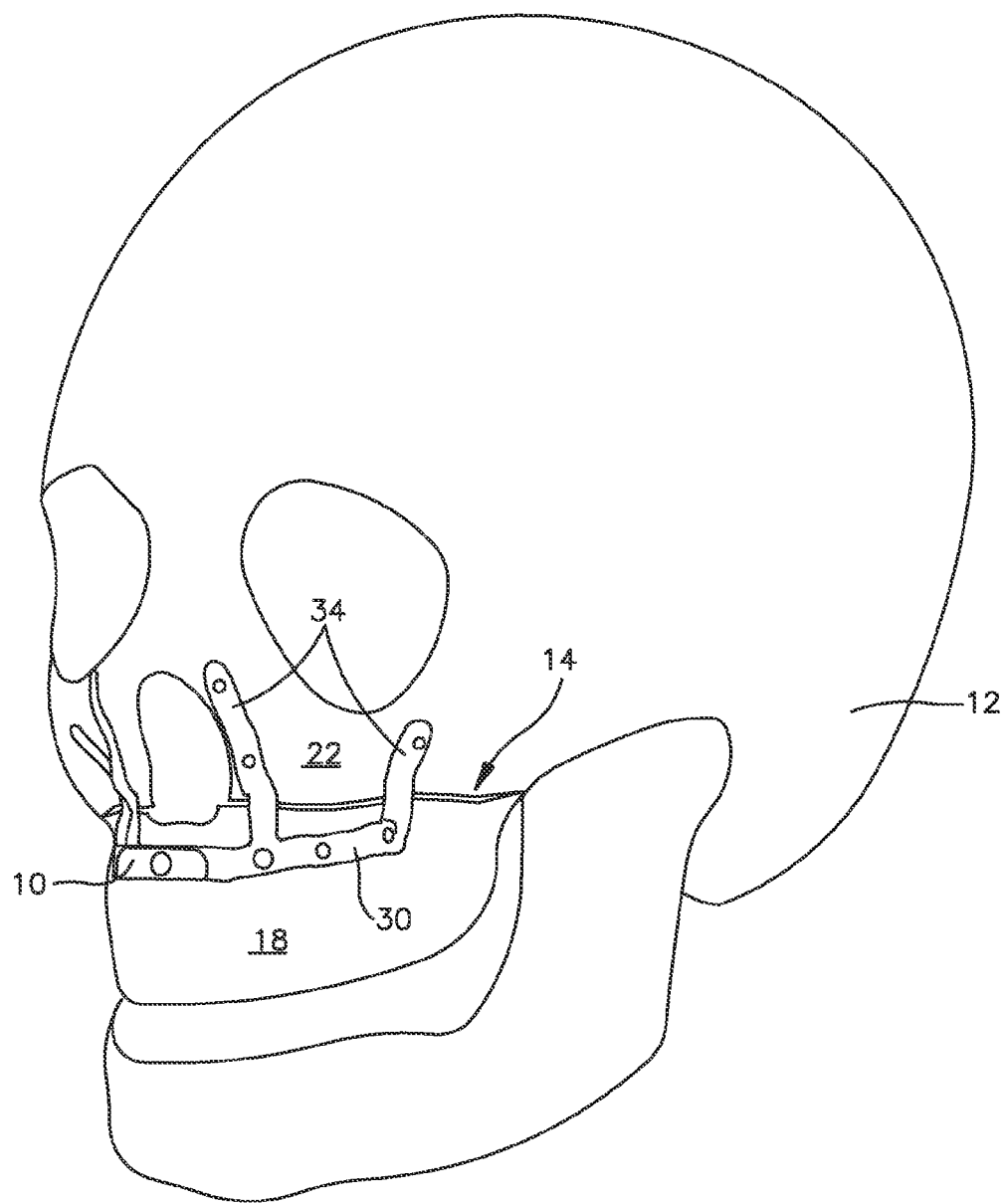
FIG. 1 is a perspective view of a skull with a bone fixation implant affixed to the maxilla.

Referring to FIG. 1 a bone fixation implant 10 to be used in orthognathic surgery is designed to be fixed to underlying bone such as a patient's skull 12, and in particular to a patient's maxilla 14 after the maxilla 14 has been separated into a first "segmented" part 18 and a second "integral" part 22 by a segmentation procedure, such as an osteotomy. The first part 18 of the maxilla 14 typically carries the upper teeth and is completely separated from the skull 12 after the osteotomy has been performed, while the second part 22 of the maxilla 14 remains intact with the skull 12. The bone fixation implant 10 is configured to attach to the first and second parts of the maxilla, and thereby support and hold the first part 18 of the maxilla relative to the second part 22 while osteogenesis occurs. The implant 10 is customized pre-operatively to minimize complications during surgery and time spent in the operating room by a patient.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases designate preferred positions and orientations in the human body to which reference is made and are not meant to be limiting. The terminology includes the above-listed words, derivatives thereof and words of similar import.

Referring to FIGS. 2A-2D, the implant 10 and various components of the implant are described herein extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. When the implant 10 is implanted onto a maxilla, such as the maxilla 14, the transverse direction T extends vertically generally along the superior-inferior (or caudal-cranial) direction, while the plane defined by the longitudinal direction L and lateral direction A extends horizontally, generally in the anatomical plane defined by the medial-lateral direction and the anterior-posterior direction. Accordingly, the directional terms "vertical" and "horizontal" are used to describe the implant 10 and its components as illustrated merely for the purposes of clarity and illustration.

As shown in FIGS. 2A-2D, the bone fixation implant 10 includes a longitudinal plate member 30 that is elongate and curved in the longitudinal direction L and a holding structure 34 that extends vertically from the longitudinal member 30. The longitudinal plate member 30 includes an upper edge 38, a bone engaging surface configured to lie substantially flush with the maxilla, and an outer surface opposed to the bone engaging surface. Therefore, the holding structure 34 extends up from the upper edge 38 of the longitudinal member 30. As shown in FIG. 1, the bone fixation implant 10 supports and holds the first part 18 of the maxilla relative to the second part 22 while osteogenesis occurs. The bone fixation implant 10 and components thereof, can be formed from a variety of biocompatible materials, such as cobalt chromium molybdenum (CoCrMo), titanium, and titanium alloys, stainless steel, ceramics, or polymers such as polyetheretherketone (PEEK), polyetherketoneketone (PEKK), and bioresorbable materials. A coating may be added or applied to the bone fixation implant 10 to improve physical or chemical properties or to provide medications. Examples of coatings include plasma-sprayed titanium coating or Hydroxyapatite.

Figure 2A:
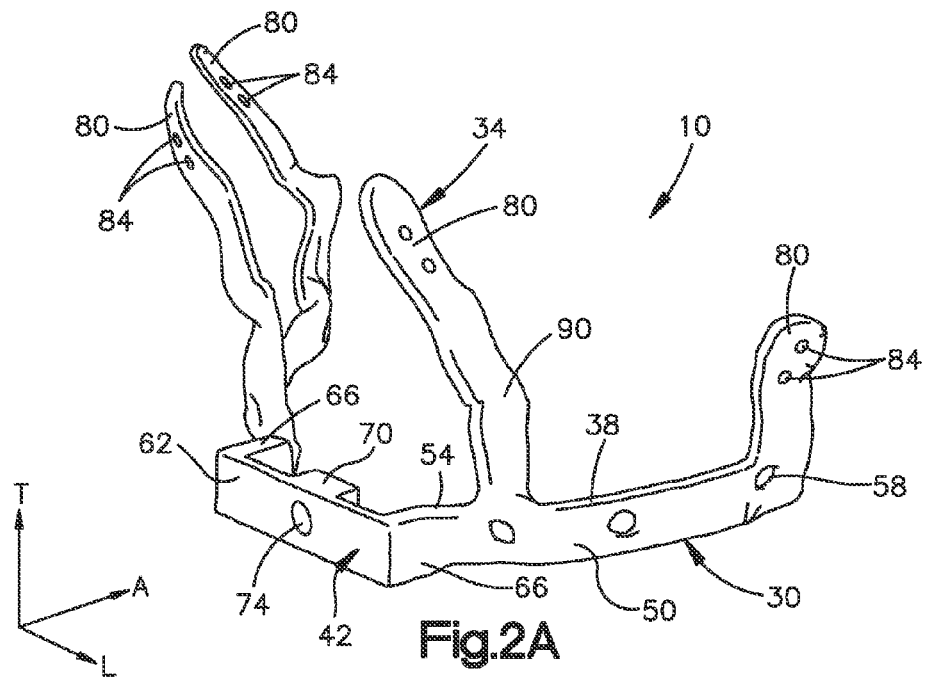
FIG. 2A is a perspective view of a bone fixation implant constructed in accordance with one embodiment.
Figure 2B:
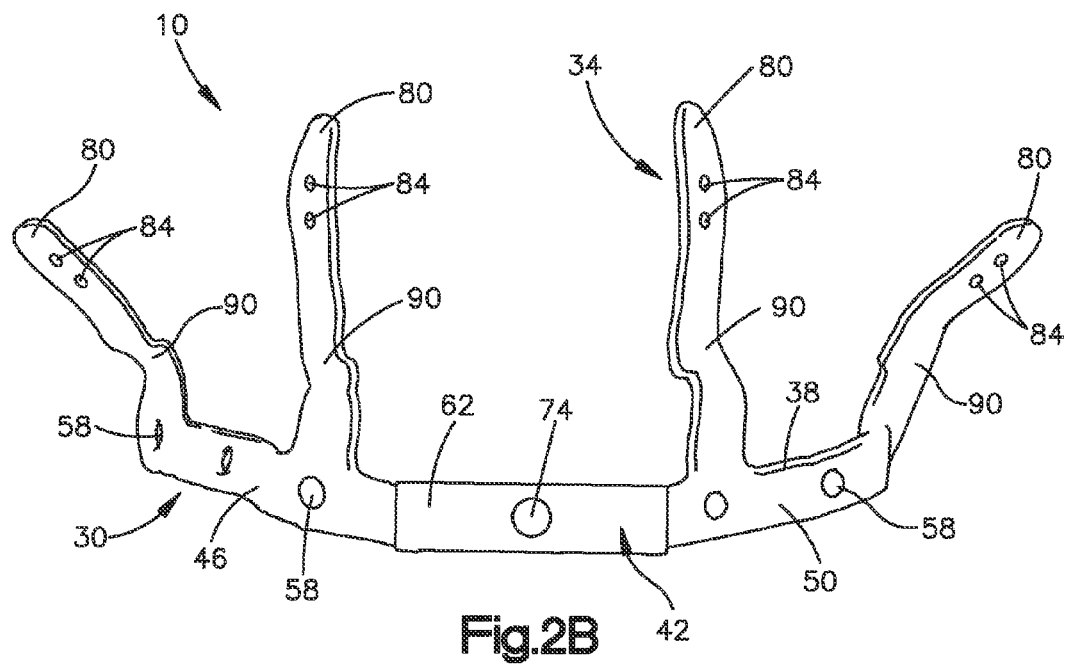
FIG. 2B is a front elevation view of the bone fixation implant shown in FIG. 2A.
Figure 2C:
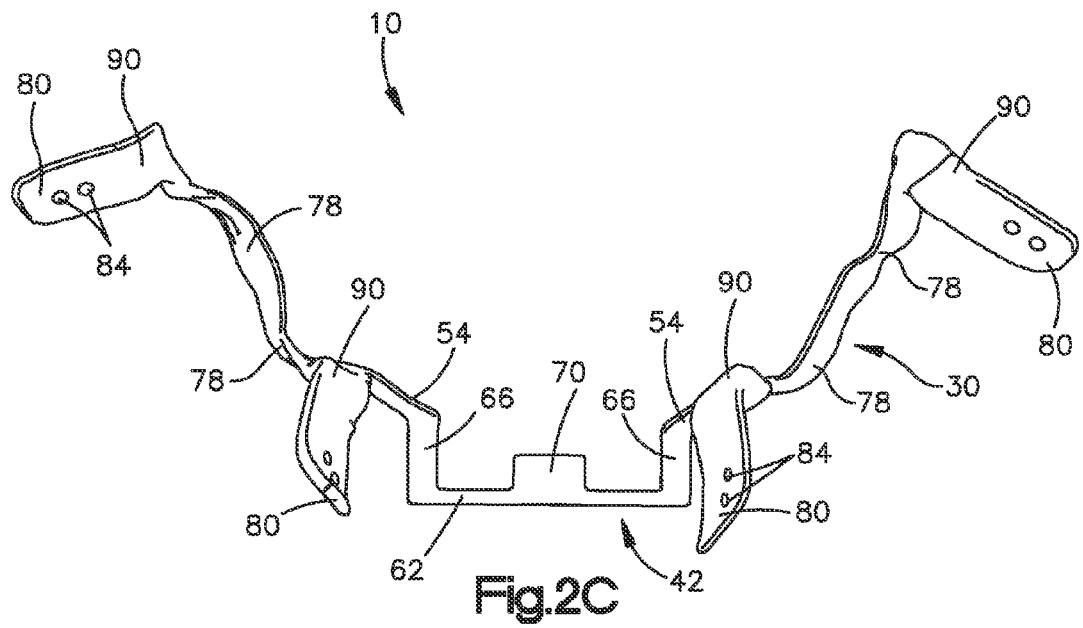
FIG. 2C is a top plan view of the bone fixation implant shown in FIG. 2A.
Figure 2D:
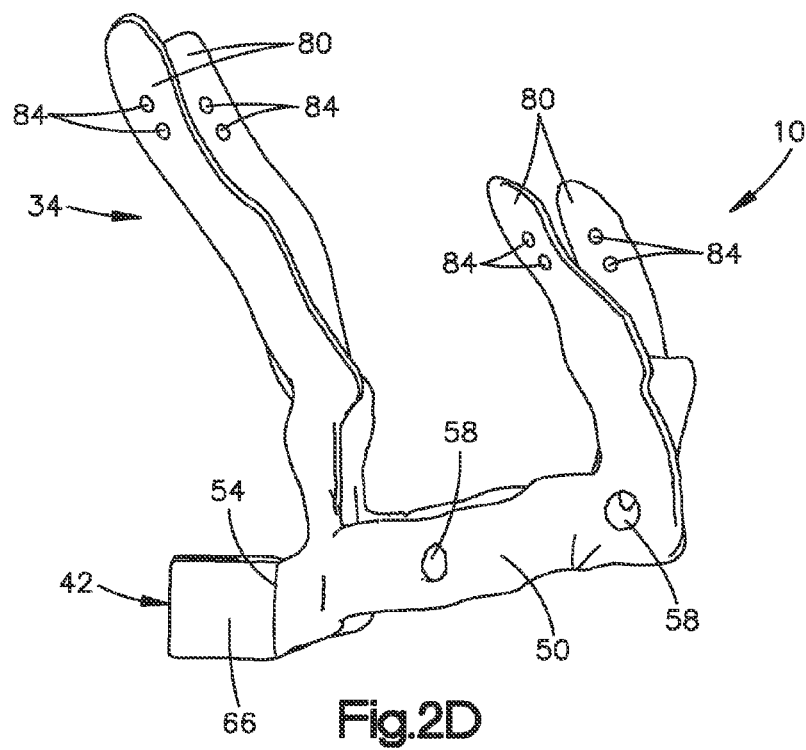
FIG. 2D is a left side elevation view of the bone fixation implant shown in FIG. 2A.

As shown in FIGS. 1, and 2A-2D, the longitudinal member 30 is configured to be attached to the first part 18 of the maxilla 14. In general, the longitudinal member 30 includes a central bridge member 42 that separates the longitudinal member 30 into a first portion 46 and a second portion 50. The first and second portions 46, 50 extend from the bridge member 42 from respective junctions 54. As shown, the first portion 46 extends from the bridge member 42 in a first direction, while the second portion 50 extends from the bridge member 42 in a second direction that is generally opposite to the first direction. As best shown in FIG. 2C, the first portion 46 and the second portion 50 each curves in the lateral direction A as they extend longitudinally. Therefore, as best shown in FIG. 2C, the longitudinal member 30 is curved such that it forms generally a C-shaped structure. Furthermore, as best shown in FIGS. 2B and 2D, the first portion 46 and the second portion 50 each angle up in the transverse direction T as they extend longitudinally. The curvature and shape of the longitudinal member 30 generally correspond to the shape of the maxilla 14.

Additionally, the first and second portions 46, and 50 of the longitudinal member 30 include a plurality of fixation element receiving apertures/holes 58 that extend from the outer surface of the longitudinal member 30 and through to the bone engaging surface. Each hole 58 is configured to receive a fixation element, such as a screw. Though it should be understood that any fixation element will suffice. The implant 10 is configured to be fastened to the first part 18 of the maxilla 14 by inserting fixation elements through each hole 58 of the longitudinal member 30 and into the first part 18 of the maxilla 14.

The bridge member 42 of the longitudinal member 30 includes a plate 62 that is elongate in the longitudinal direction L, an extension 66 extending in the lateral direction A from each end of the plate 62, and a centrally located protrusion 70 that also extends laterally from an inner surface of the plate 62. The junctions 54 are located at the posterior ends of each extension 66. Thus, the first and second portions 46, 50 of the longitudinal member 30 each extend from a posterior end of a respective extension 66 of the bridge member 42. The bridge member 42 may be removed from the longitudinal member 30 at the junctions 54 once the implant 10 is secured to the maxilla 14. The junction points 54 may be weakened so that the bridge member 42 may be easily removed once the implant 10 is secured to the maxilla 14. For example, junctions 54 may be thinned, or perforated, or otherwise configured, so that the bridge member 42 may be removed by snapping the bridge member 42 away. It should be understood however that the bridge member 42 may be removed by cutting the junction points 54 with snips or pliers. Because the bridge member 42 is removable, the amount of the implant 10 left in the patient may be minimized.

As shown in FIG. 2B, the bridge member further includes a reference hole 74 that extends laterally through both the plate 62 and the protrusion 70 of the bridge member 42. The implant 10 may initially be fastened to the maxilla 14 by inserting a fixation element through the reference hole 74 and into the maxilla 14. The fixation element inserted into the reference hole 74 may temporarily affix the implant 10 to the maxilla 14 while a surgeon correctly aligns the implant 10 for complete fixation to the maxilla 14.

The longitudinal member 30 and in particular the first and second portions 46, 50, is pre-shaped to correspond to the post-operative shape of the first part 18 of the maxilla 14. In this regard the longitudinal member is pre-shaped prior to the segmentation procedure, so as to correspond to an outer surface of the first part of the maxilla after the segmentation procedure. While it is preferable that the member 30 is pre-shaped such that no manual bending is required prior to placement of the implant 10 onto the maxilla 14, the member 30 may be pre-shaped such that only minimal bending is required prior to placement of the implant 10 onto the maxilla 14 (e.g. bending that may take place when fastening the member 30 to the maxilla 14). As best shown in FIG. 2C, the first and second portions 46, 50 include several non-linear undulations 78 that correspond to particular surface portions of the first part 18 of the maxilla 14. It should be understood, however, that the shape of the first part 18 of the maxilla 14 may be unchanged between the pre-operative and post-operative shape of the maxilla 14. Therefore, the longitudinal member 30 may be pre-shaped to correspond to both the pre-operative shape and the post-operative shape of the first part 18 of the maxilla 14.

As shown in FIGS. 2A-2D, the holding structure 34 of the implant 10 includes at least one finger 80, such as a plurality of fingers 80 that extend up from the upper edge 38 of the longitudinal member 30. In accordance with the illustrative embodiment, two fingers 80 extend from each of the first and second portions 46, and 50 of the longitudinal member 30. However, it should be understood that any number of fingers 80 may extend up from the first and second portions 46, and 50. As shown, each finger 80 includes at least one fixation element receiving aperture or hole 84 configured to receive a fixation element, such as a screw, so as to affix the fingers 80 to the second part 22 of the maxilla 14. Though it should be understood any fixation element will suffice. While the embodiment illustrated shows each finger 80 having two holes 84, it should be understood, that each finger may have any number of holes, e.g. 1, 2, 3, 4, etc.

As best shown in FIG. 2B, the fingers 80 are spaced apart along the first and second portions 46, 50 of the longitudinal member 30 and extend substantially perpendicularly relative to the point on the portions 46, 50 from where they extend. That is, the longitudinal plate member 30 is non-linear and will define tangents at different points along its edge 38. Therefore, each finger 80 will extend perpendicular with respect to a tangent taken at the point on the edge 38 from which the finger 80 extends. Though it should be understood that the fingers 80 do not have to extend perpendicularly, and may extend at some angle relative to the longitudinal member 30. Preferably, each finger 80 extends from the longitudinal member 30 such that a fixation element hole 58 of the longitudinal member 30 is aligned with the point at which a respective finger 80 extends from the edge 38 of the longitudinal member 30, to further improve equal force distribution throughout the implant 10.

The holding structure 34 or fingers 80 are pre-shaped to correspond to the post-operative shape of the second part 22 of the maxilla 14, and extend from the first and second portions 46, 50, so as to provide a fixation member that corresponds to the shape and the relationship of the first parts of the maxilla. In this regard the fingers 80 are pre-shaped prior to the segmentation procedure, so as to correspond to an outer surface of the second part of the maxilla after the segmentation procedure. While it is preferable that the fingers 30 are pre-shaped such that no manual bending is required prior to placement of the implant 10 onto the maxilla 14, the fingers 80 may be pre-shaped such that only minimal bending is required prior to placement of the implant 10 onto the maxilla 14. Therefore, as best shown in FIG. 2C, the fingers 80 include several non-linear undulations 90 that correspond to particular surface portions of the second part 22 of the maxilla 14. Because the fingers 80 are pre-shaped, they will fit correctly only at the desired location of the maxilla 14 and provide a surgeon with positive assurance that they have achieved correct alignment and, therefore, a desired corrected shape.

Before the implant 10 is affixed to the maxilla, an osteotomy is performed to separate the maxilla 14 into the first part 18 and the second part 22. A temporary osteotomy guiding implant 110 may be affixed to the maxilla 14 before the osteotomy is performed on the maxilla 14 to create a guide for the surgeon. In particular, the osteotomy guiding plate 110 provides a template for a surgeon to follow while performing the osteotomy. For example, the osteotomy guiding implant 110 allows the surgeon to make guide holes in the maxilla to follow while performing the osteotomy. In this way, the osteotomy guiding implant acts as a drill guiding implant. The osteotomy guiding implant also provides a template for the surgeon to follow while implanting the bone implant 10. The osteotomy guiding implant 110 is also customized pre-operatively to minimize complications during surgery and time spent in the operating room by a patient.

As shown in FIGS. 3A-3D, the osteotomy guiding implant 110 includes a longitudinal plate member 130 that is elongate and curved in the longitudinal direction L, and a template portion 132 that includes a plurality of fingers/protrusions 134 that extend vertically in the transverse direction T from the longitudinal member 130. Like the implant 10, the osteotomy guiding implant 110 includes an upper edge 138, a bone engaging surface configured to lie substantially flush with the maxilla, and an outer surface opposed to the bone engaging surface. The osteotomy guiding implant 110 and components thereof, can be formed from a variety of biocompatible materials, such as cobalt chromium molybdenum (CoCrMo), titanium, and titanium alloys, stainless steel, ceramics, or polymers such as polyetheretherketone (PEEK), polyetherketoneketone (PEKK), and bioresorbable materials. A coating may be added or applied to the osteotomy guiding implant 110 to improve physical or chemical properties or to provide medications. Examples of coatings include plasma-sprayed titanium coating or Hydroxyapatite.

Figure 3C:
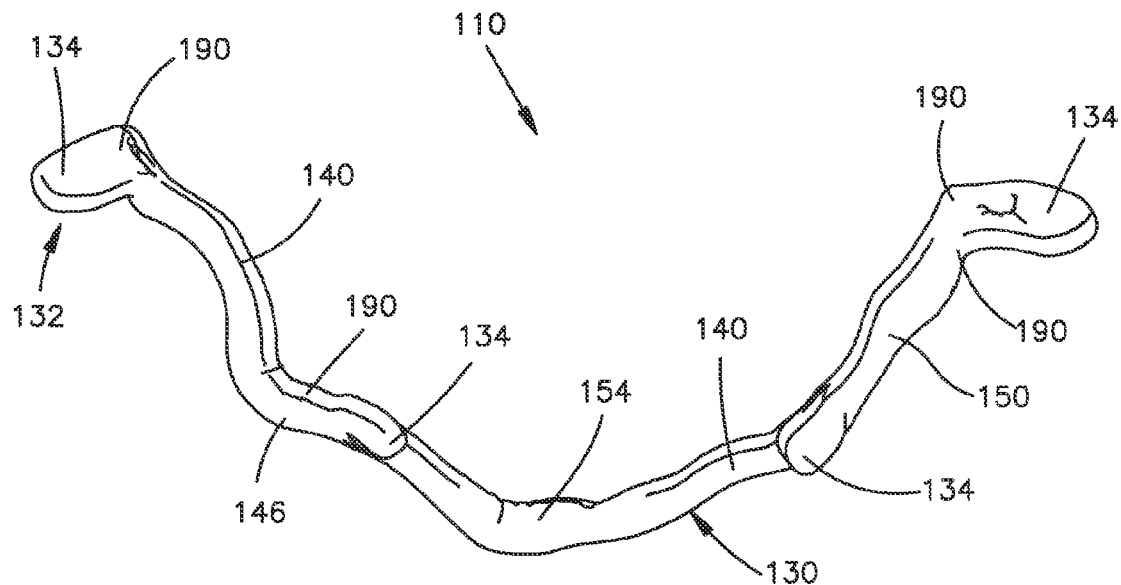
FIG. 3C is a top plan view of the osteotomy guiding implant shown in FIG. 3A.
Figure 3D:
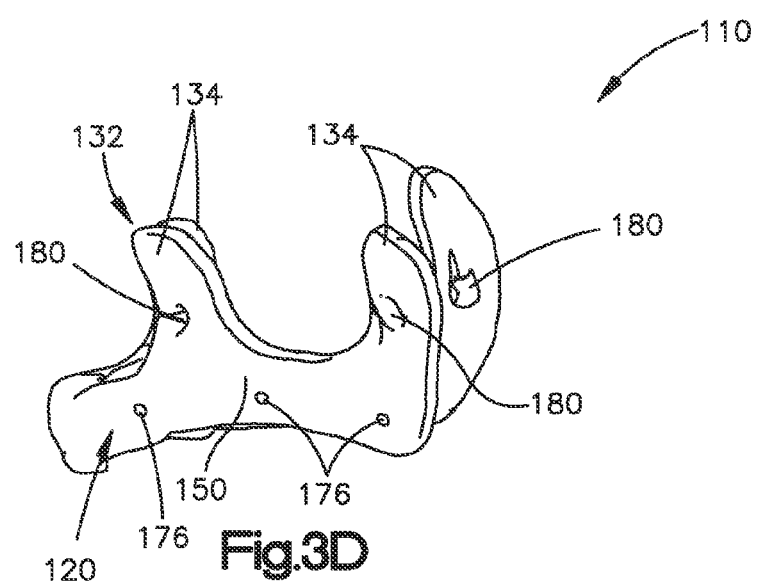
FIG. 3D is a left side elevation view of the osteotomy guiding implant shown in FIG. 3A.

As best shown in FIG. 3C, the longitudinal plate member 130 includes a first portion 146 and a second portion 150 that extend in opposite directions from a central juncture 154. Each portion 146 and 150 curves in the lateral direction A as it extends longitudinally. Therefore, as shown in FIG. 3C, the longitudinal member 130 is curved such that it forms generally a C-shaped structure similar to the bone fixation implant 10. Furthermore, as best shown in FIGS. 3B and 3D, the first portion 146 and the second portion 150 each angle up in the transverse direction T as they extend longitudinally. The curvature and shape of the longitudinal member 130 should be configured to correspond to the shape of the maxilla 14.

As shown in FIG. 3B, the longitudinal plate member 130 further includes a reference hole 174 that extends through the plate member 130 proximate to the central juncture 154 from the outer surface to the bone engaging surface. The osteotomy guiding implant 110 may initially be fastened to the maxilla 14 by inserting a fixation element through the reference hole 174 and into the maxilla 14. The fixation element inserted into the reference hole 174 may be temporary and is utilized while a surgeon correctly aligns the implant 110 so that an osteotomy guide may be created.

As shown in FIGS. 3A-3D, the longitudinal plate member 130 defines a plurality of apertures or holes 176. As best shown in FIG. 3B, the embodiment illustrated includes three holes 176 in each portion 146 and 150. The holes 176 are spaced apart and provide a template for the surgeon to drill pre-holes into the maxilla 14 that will align with the holes 58 defined by the longitudinal member 30 of the bone implant 10. Therefore, the surgeon will know where to secure the bone implant 10 to the first part 18 of the maxilla 14 after the osteotomy is performed by aligning the holes 58 of the bone implant 10 with the pre-drilled holes. Though it should be understood that in some cases, the longitudinal plate member 130 does not have the apertures 176, and thus the pre-drilled holes are not required to properly align the bone implant 10.

As shown in FIGS. 3A-3D, the osteotomy guiding implant's fingers 134 extend up from the upper edge 138 of the longitudinal member 130. In particular, two fingers 134 extend from each of the first and second portions 146, and 150 of the longitudinal member 130. However, it should be understood that any number of fingers 134 may extend up from the first and second portions 146, and 150.

As best shown in FIG. 3B, the fingers 134 are spaced apart along the longitudinal member 130 and extend substantially perpendicularly relative to the point on the longitudinal member 130 from where they extend. That is, the longitudinal member 130 is non-linear and will define tangents at different points along its edge 138. Therefore, the fingers 134 extend perpendicular with respect to a tangent taken at the point on the edge 138 from which the finger 134 extends. Though it should be understood that the fingers 134 do not have to extend perpendicularly and may extend at an angle relative to the longitudinal member 130.

As shown in FIG. 3B, each finger 134 of the osteotomy guiding implant 110 defines an aperture or hole 180. The holes 180 are configured to receive a drill bit so that guide holes may be drilled into the maxilla 14 to thereby define a guide path along which the osteotomy may be performed. As shown, the holes 180 of the fingers 134 will be positioned such that the guide path along which the osteotomy will be performed is appropriately located so that the bone fixation implant 10 may securely hold the first part 18 of the maxilla 14 relative to the second part 22. That is, the osteotomy will be located such that the fingers 80 of the bone implant 10 will be long enough to extend across the osteotomy to securely hold the first part 18 of the maxilla relative to the second part 22.

The osteotomy guiding implant 110, and in particular the longitudinal member 130 and the fingers 134, is pre-shaped to correspond to the pre-operative shape, and relative position of the first part 18 and the second part 22 of the maxilla 14. As best shown in FIG. 3C, the longitudinal member 130 and the fingers 134 include several non-linear undulations 190 that correspond to particular portions of the first part 18 and the second part 22 of the maxilla 14.

Figure 4:
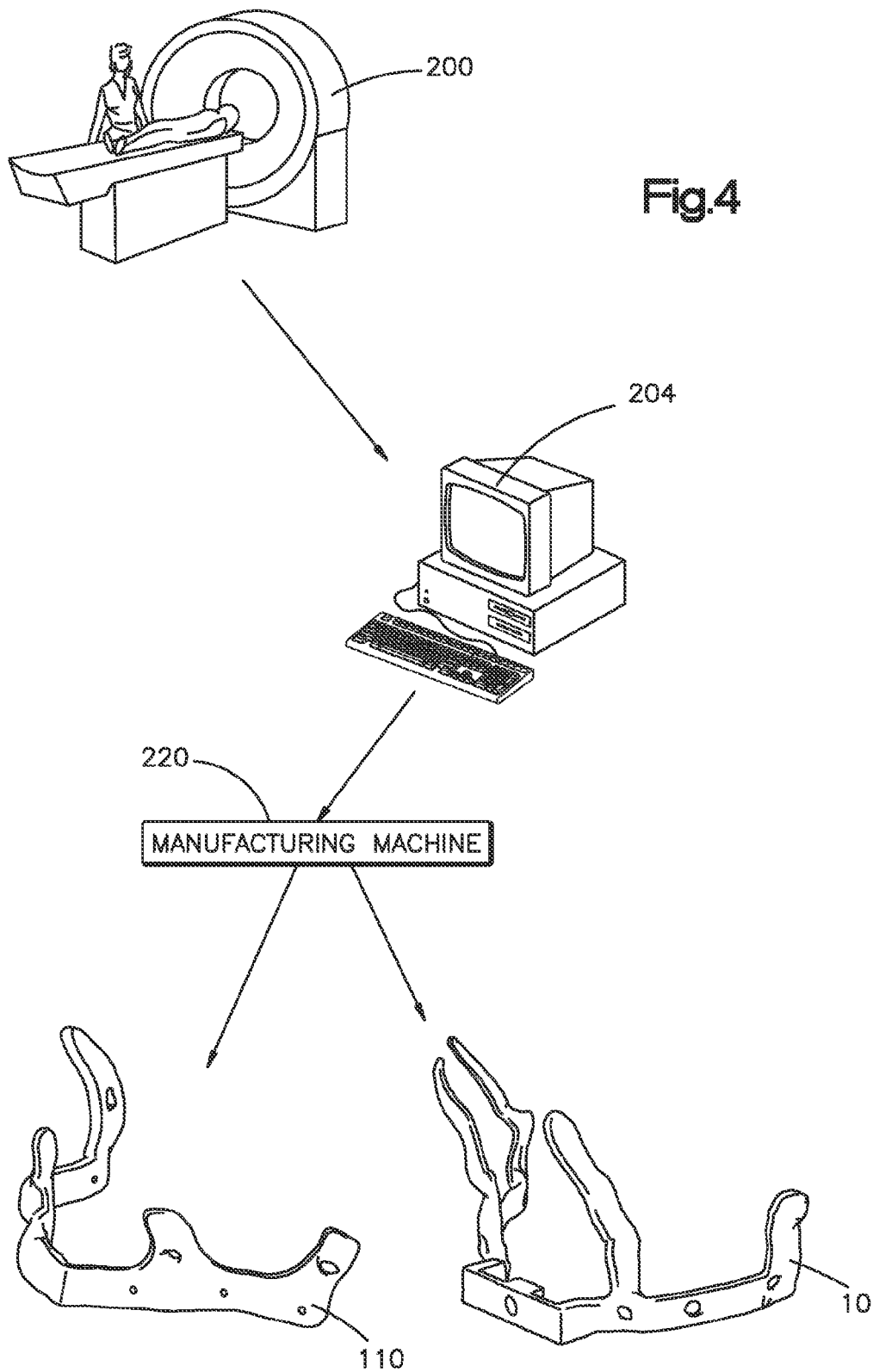
FIG. 4 is a diagram showing the process for customizing the bone fixation implant of FIGS. 2A-2D and the osteotomy guiding implant of FIGS. 3A-3D to correspond to an individual patient's maxilla.

In reference to FIG. 4, both the bone fixation implant 10 and the osteotomy guiding implant 110 are manufactured and shaped pre-operatively. Prior to the orthognathic surgery being performed, a 3-D image of the patient's skull, and in particular the patient's maxilla, such as maxilla 14 is obtained. This may be completed with a CT scanning device 200 or the like, with slices smaller than 1 mm preferred, and optimally between 0.2-1 mm. A high resolution for the slices is preferred, since the exact shape of the maxilla 14 should be determined from the CT scan slices. It will be appreciated that other scanning devices 200 besides a CT scanning device may be used so long as they provide three dimensional data corresponding to the shape of the maxilla 14.

Once the 3-D image of the patient's skull/maxilla is obtained, the image is loaded into a computer 204 to create a virtual model of the skull for manipulation by a user such as the surgeon. The computer 204 may be local (same general area as the CT scanning device 200) or remote where the image must be sent via a network. Similarly, the image loaded onto the computer 204 may be manipulated by a user that is working locally or remotely. Typically, however, the image is manipulated remotely by the surgeon who will be performing the orthognathic surgery.

The virtual model of the skull may be manipulated by the surgeon using standard software typical in the art. For example, Mimics, a software commercially available from Materialise, having a place of business in Leuven Belgium, may be used to process and manipulate the virtual model obtained from the CT scanning device 200. The software allows the surgeon to analyze the patient's maxilla and pre-operatively plan the patient's orthognathic surgery including the shape and design of the bone fixation implant a and an osteotomy guiding implant.

Using the virtual model of the patient's skull/maxilla, the surgeon may first make a virtual model of an osteotomy guiding implant, such as the osteotomy guiding implant 110 shown in FIGS. 3A-3D. This is accomplished by determining on the virtual model of the skull where the osteotomy is to be performed, and then actually performing a virtual osteotomy on the virtual model. Once the virtual osteotomy is complete, the surgeon can begin making the virtual model of the osteotomy guiding implant 110. At this point, it should be understood that the virtual model of the skull and in particular the maxilla still has its pre-operative shape and position. Therefore, the longitudinal plate member 130 and the fingers 134 of the osteotomy guiding implant 110 that is being made will correspond to the pre-operative shape of the patient's maxilla. The holes 180 that are formed in the fingers 134 of the osteotomy guiding implant 110 will be made in the virtual model to correspond to the virtual osteotomy that was performed on the virtual model of the skull. Therefore, the osteotomy guiding implant 110 manufactured using the virtual model, will define holes 180 that create a guide path for the surgeon to follow while performing the osteotomy. In this way, the actual osteotomy performed on the patient will match the virtual osteotomy that was performed on the virtual model.

After the virtual model of the osteotomy guiding implant 110 is complete, the surgeon or other operator may manipulate the first part 18 (the cut off portion) of the virtual model of the maxilla 14 from a first undesired position to a second desired position. Once the first part 18 is positioned and the virtual model portrays the post-operative shape and position of the patient's maxilla, as approved by the surgeon, a virtual model of a bone fixation implant, such as the bone fixation implant 10 shown in FIGS. 2A-2D, can be made. At this point, it should be understood that the virtual model of the skull and in particular the maxilla has a post-operative shape and position. Therefore, the longitudinal plate member 30 and the fingers 80 of the bone fixation implant 10 that is being made will correspond to the post-operative shape of the patient's maxilla.

The virtual models of the osteotomy guiding implant 110 and the bone fixation implant 10 may be downloaded or transferred from the computer 204 to a CAD/CAM milling/manufacturing machine 220 or the like. The manufacturing machine 220 will machine the osteotomy guiding implant 110 and the bone fixation implant 10 out of any desired material. Once the osteotomy guiding implant 110 and the bone fixation implant 10 have been manufactured, the surgeon may begin the orthognathic surgery on the patient.

Figure 5A:
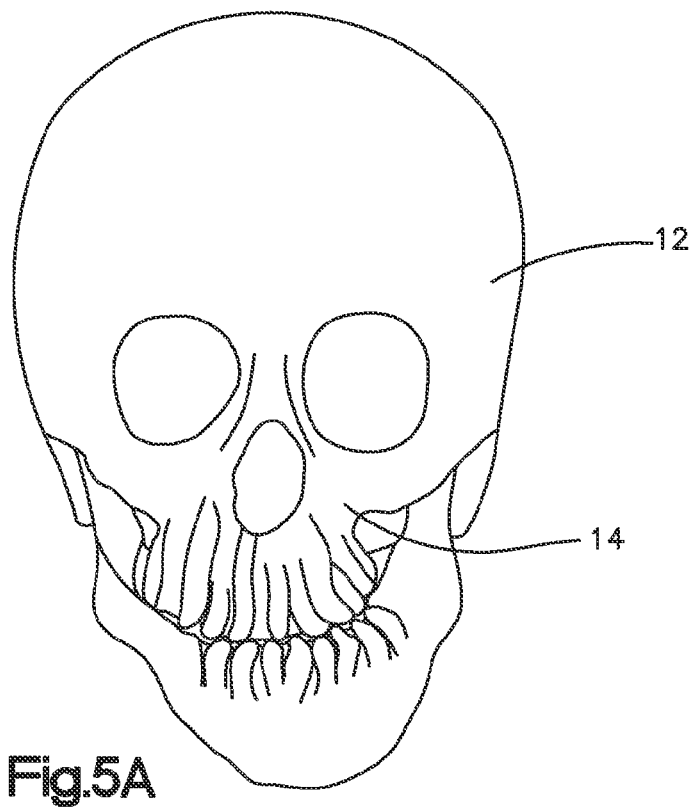
Figure 5B:
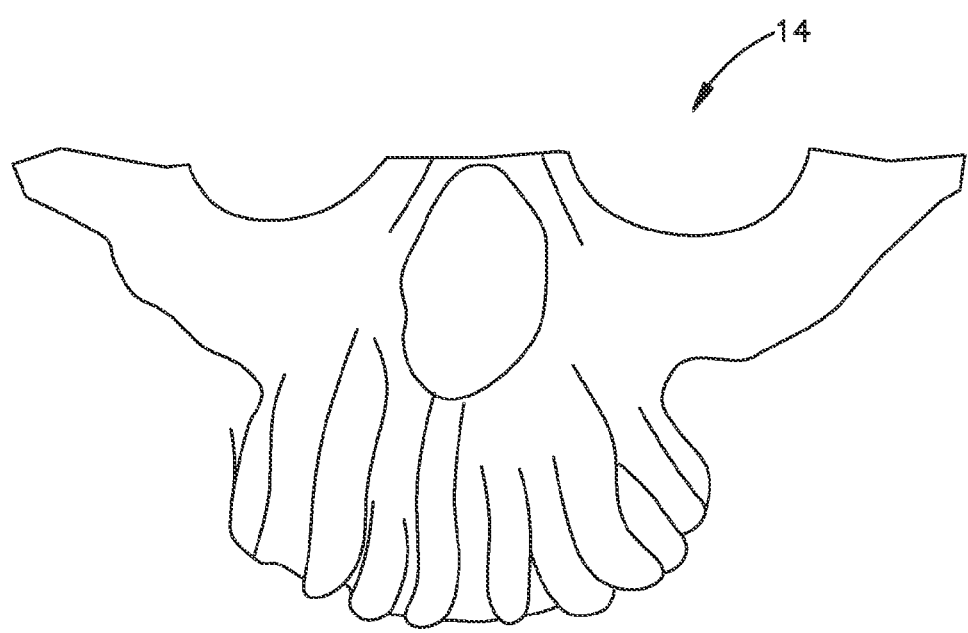
FIG. 5B is an enlarged detailed view showing the pre-operative shape of the maxilla of the skull shown in FIG. 5A.

FIGS. 5A-5J show an example method of performing an orthognathic surgery using the osteotomy guiding implant 110 and the bone fixation implant 10. It should be understood that prior to the surgery, the osteotomy guiding implant 110 and the bone fixation implant 10 are pre-shaped to substantially correspond to the individual patient's maxilla. FIG. 5A shows an example skull 12 having a maxilla 14 that needs to be repositioned. FIG. 5B is a detailed view of the maxilla 14 shown in FIG. 5A. As shown, the maxilla 14 at this point has a pre-operative shape. An osteotomy is to be performed on the maxilla 14 to thereby separate the maxilla 14 into a first part 18 and a second part 22, so that the first part 18 can be repositioned, as will be described below.

Figure 5C:
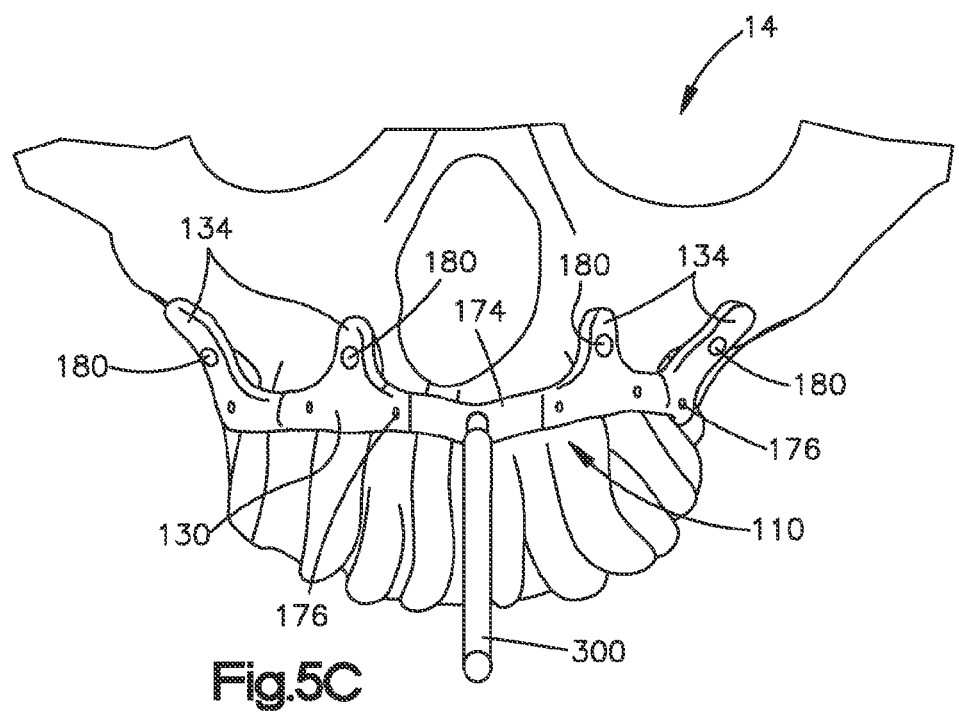
FIG. 5C is a front elevation view of the maxilla shown in FIG. 5B, showing the osteotomy guiding implant of FIGS. 3A-3D being attached to the maxilla.

As shown in FIG. 5C, the osteotomy guiding implant 110 may be placed onto the maxilla 14. As stated before, the osteotomy guiding implant 110 is pre-shaped to correspond to the pre-operative shape of the maxilla 14, and therefore will lie flush against the maxilla 14. In other words both the longitudinal plate member 130 and the fingers 134 will be pre-shaped to correspond to the pre-operative shape of the maxilla 14. Once properly positioned, the osteotomy guiding implant 110 may be temporarily affixed to the maxilla 14 by inserting a screw 300 into the reference hole 174 of the osteotomy guiding implant 110 and screwing it into the maxilla 14 with a driver 300.

Figure 5D:
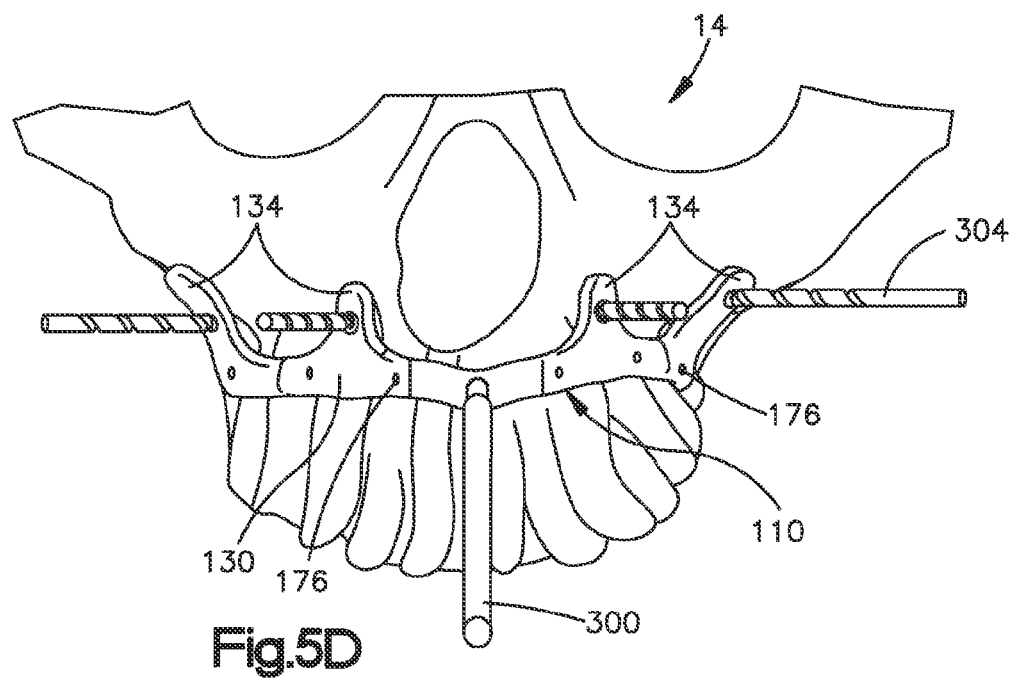
FIG. 5D is a front elevation view of the of the maxilla shown in FIG. 5C, showing holes being drilled into the maxilla through guide holes defined by the osteotomy guiding implant.
Figure 5E:
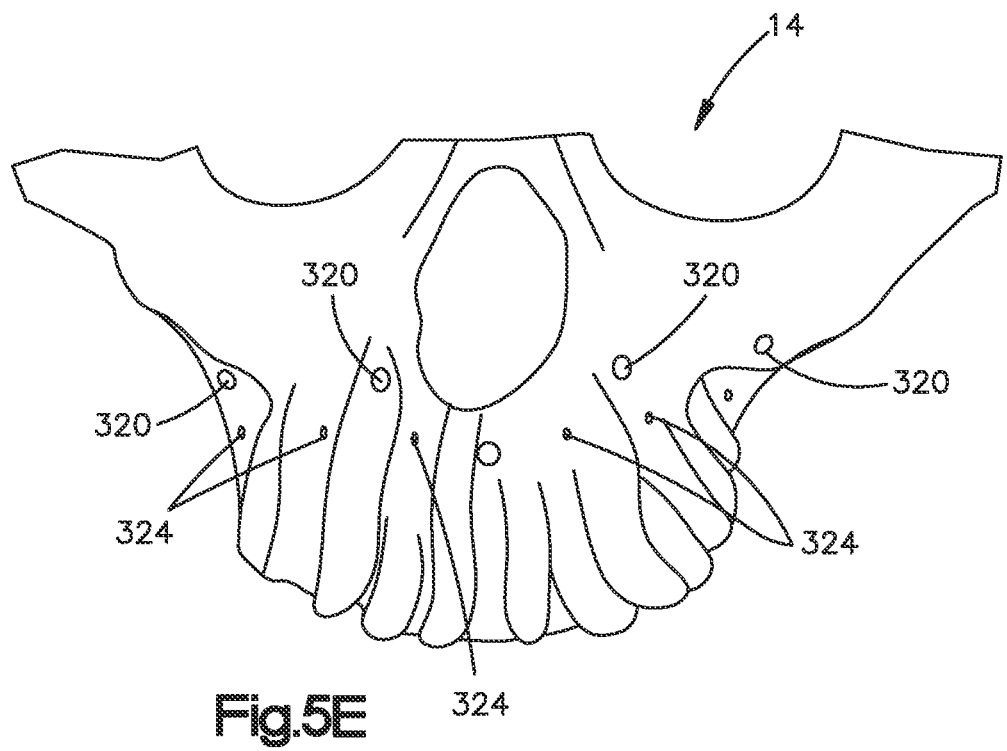
FIG. 5E is a front elevation view of the maxilla shown in FIG. 5D, showing the drilled holes.

As shown in FIG. 5D, the surgeon may then drill holes into the maxilla 14 using a drill bit 304. As shown, the drill bit 304 may be inserted into the holes 180 defined by the fingers 134 of the osteotomy guiding implant 110. As stated before, the holes 180 are pre-planned and positioned so that the surgeon can create a cutting path for the surgeon to follow while performing the osteotomy. For example, as shown in FIG. 5E, four holes 320 are drilled into maxilla 14 using the osteotomy guiding implant 110. While four holes 320 are shown, it should be understood that the osteotomy guiding implant 110 may be configured so that any number of holes 320 may be made using the osteotomy guiding implant 110. For example, the osteotomy guiding implant 110 may be made to have six fingers 134 so that six holes 320 may be made in the maxilla.

As shown in FIG. 5D, drill bit 304 or another drill bit may be inserted into holes 176 defined by the longitudinal member 130 of the osteotomy guiding implant 110. As shown in FIG. 5E, six holes 324 are drilled into the maxilla 14 using the osteotomy guiding implant 110. While six holes 324 are shown, it should be understood that the osteotomy guiding implant 110 may be configured so that any number of holes 324 may be made using the osteotomy guiding implant 110. The holes 324 will act as a guide for the surgeon to properly place the bone implant 10 to the maxilla. To ensure that bone implant 10 will be securely affixed to the maxilla 14, the holes 324 are smaller than the holes 58 defined by the bone implant 10. Thus when a screw is affixed the threads of the screw will grab a portion of the bone.

Figure 5F:
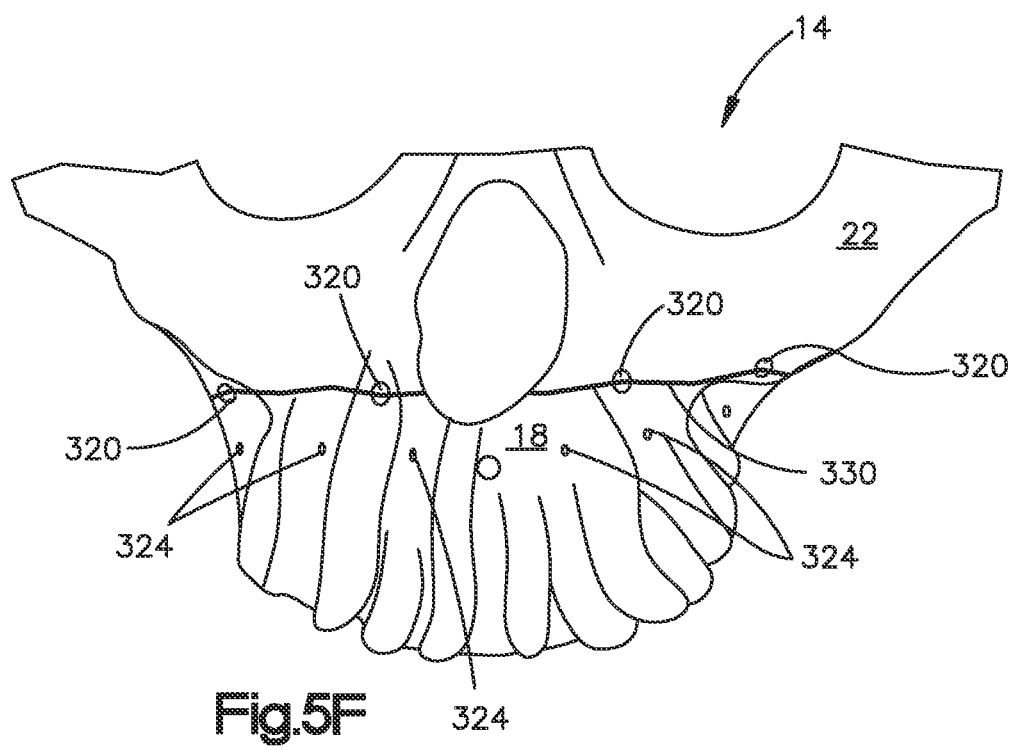
FIG. 5F is a front elevation view of the maxilla shown in FIG. 5E, showing the osteotomy performed on the maxilla, using the holes as a cutting guide.
Figure 5G:
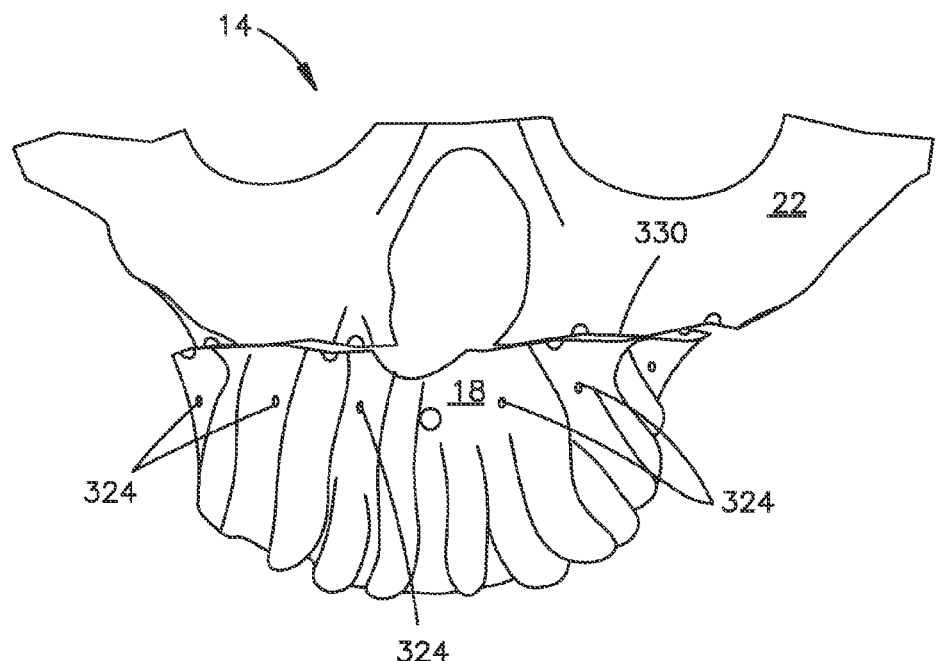
FIG. 5G is a front elevation view of the maxilla shown in FIG. 5F, showing a segmented portion of the maxilla being repositioned into a post-operative shape.

As shown in FIG. 5F, the osteotomy guiding implant 110 may be removed and the surgeon may perform an osteotomy 330 on the maxilla 14 along the cutting path created by the holes 320. In the embodiment illustrated, the cutting path extends from one hole 320 to an adjacent hole 320 until the osteotomy is complete. As shown in FIG. 5G, the osteotomy 330 separates the maxilla into a first part 18 and a second part 22. While the second part 22 remains intact with the skull, the first part 18 is free to be repositioned by the surgeon, for example as shown in FIG. 5G.

Once the first part 18 of the maxilla 14 is repositioned, the bone fixation implant 10 may be placed onto the maxilla 14. As stated before, the bone fixation implant 10 is pre-shaped to correspond to the post-operative shape of the maxilla 14, and therefore will lie flush against the maxilla 14 even after the first part 18 of the maxilla 14 has been repositioned. In other words both the longitudinal plate member 30 and the fingers 80 of the bone plate 10 will be pre-shaped to correspond to the post-operative shape of the maxilla 14. Once properly positioned, the bone fixation implant 10 may be temporarily affixed to the maxilla 14 by inserting a screw into the reference hole 74 of the bone fixation implant 10 and screwing it into the maxilla 14 with the driver 300. In most cases the reference hole 74 of the bone fixation implant 10 will line up with the hole created in the maxilla 14 by the screw that was used to temporarily affix the osteotomy guiding implant 110 to the maxilla 14.

Figure 5H:
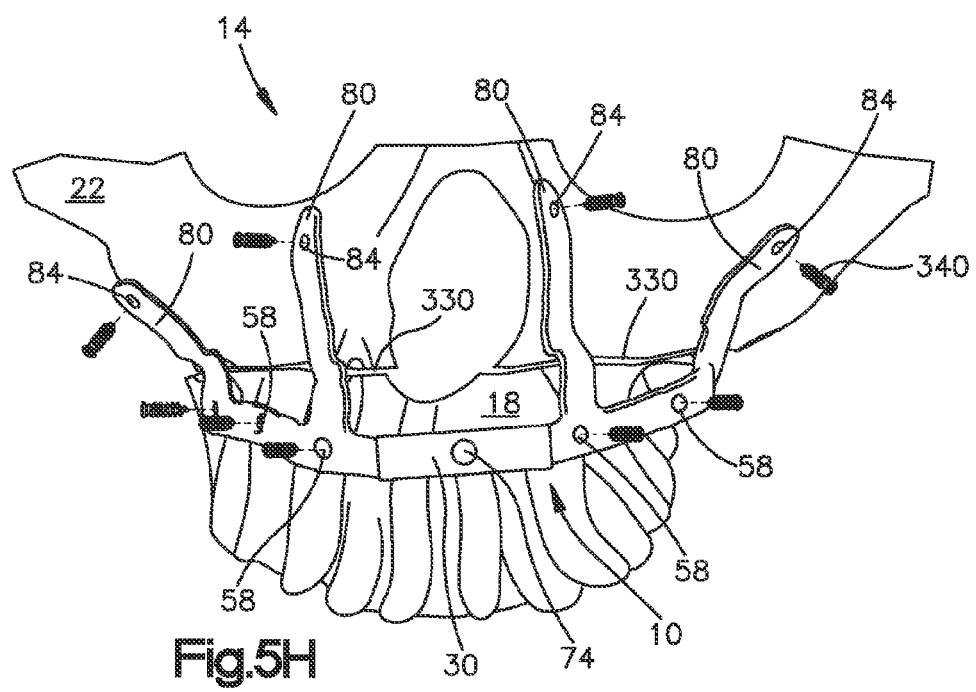
FIG. 5H is a front elevation view of the maxilla shown in FIG. 5G, showing the bone fixation implant of FIGS. 2A-2D being attached to the maxilla.
Figure 5I:
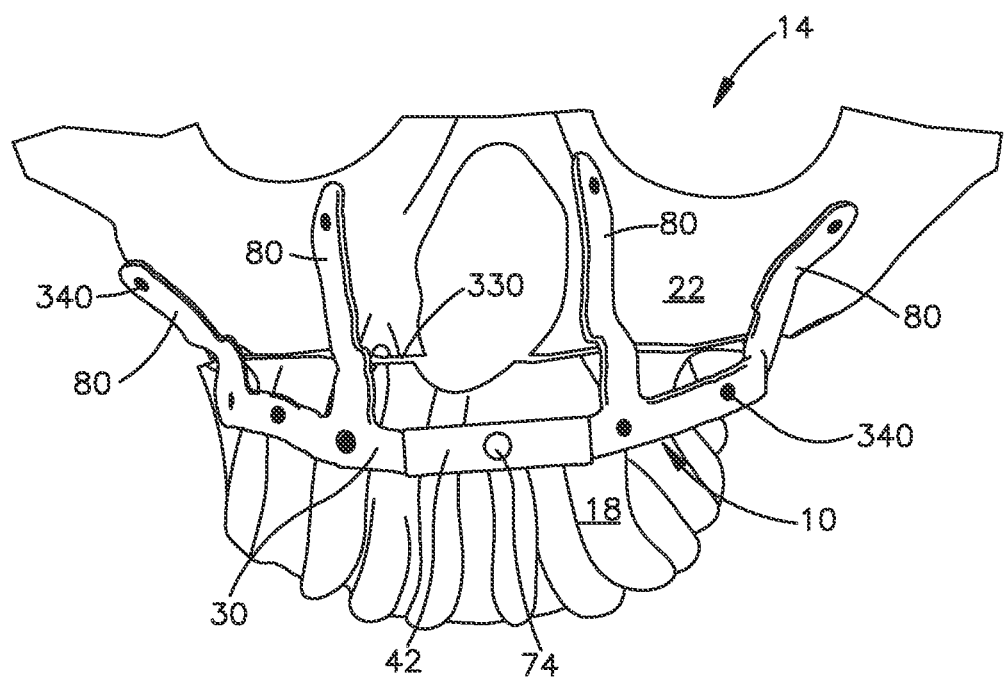
FIG. 5I is a front elevation view of the maxilla shown in FIG. 5H, showing the bone fixation implant attached to the maxilla.

As shown in FIGS. 5H and 5I, a plurality of screws 340 may be inserted into the holes 58 and the holes 84 of the bone fixation implant 10. As shown, the fingers 80 of the bone fixation implant 10 are affixed to the second part 22 of the maxilla 14 with the screws 340, and the longitudinal member 30 of the bone fixation implant 10 is affixed to the first part 18 of the maxilla 14 with the screws 340. Therefore, the bone fixation implant 10 is affixed to the maxilla 14 on either side of the osteotomy 330.

Figure 5J:
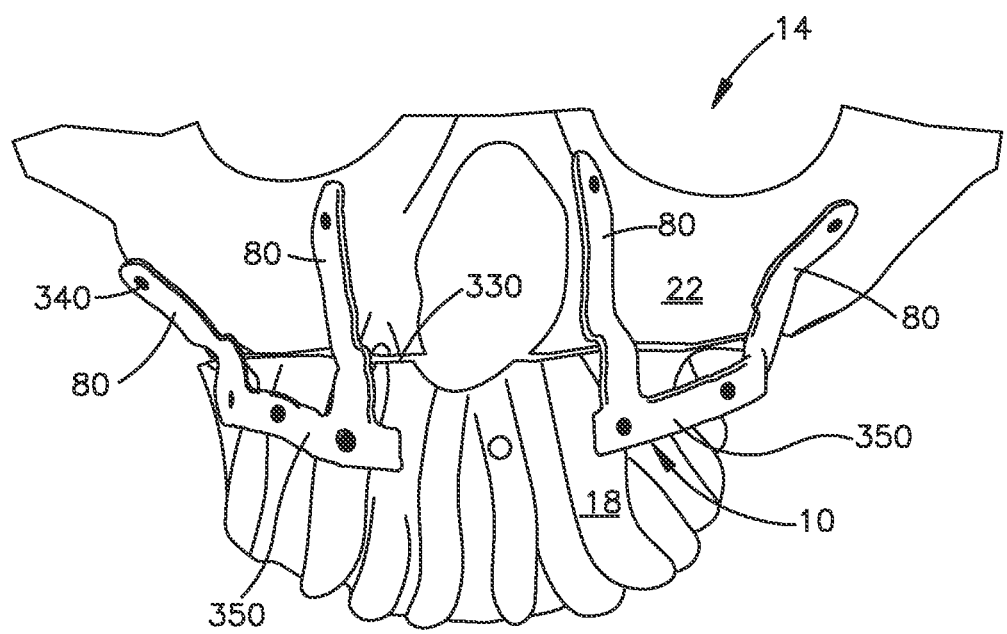
FIG. 5J is a front elevation view of the maxilla shown in FIG. 5I, showing a bridge portion of the bone fixation implant removed.

As shown in FIG. 5J, the bridge member 42 may then be removed from the bone fixation implant 10 thereby separating the bone fixation implant 10 into two separate parts 350. In this way, the bone fixation implant 10 may be considered to be a single bone fixation implant 10 that is configured to be separated into two separate implant segments or sections after the bone fixation implant 10 has been affixed to bone. As stated before, the bridge member 42 may be removed by either snapping it away or by using pliers or snips to cut the bridge member away at the junctions 54. It should be understood, however, that the bridge member 42 may be removed using any method known in the art.

Once the bridge member 42 is removed, the bone fixation implant 10 is completely installed. Therefore, the surgery may be completed, and the implant 10 may either remain within in the patient or be removed at a later time.

It should be understood that the bone fixation implant 10 and the osteotomy guiding implant 110 may be sold separately or as a kit. It should be understood, however, that the osteotomy guiding implant 110 and bone fixation implant 10 may be manufactured and delivered at different times even though they are part of the same kit. The kit may also include all of the fixation elements required to affix the bone fixation implant 10 to the maxilla 14 as well as any tools required to complete the procedure.

Figure 6:
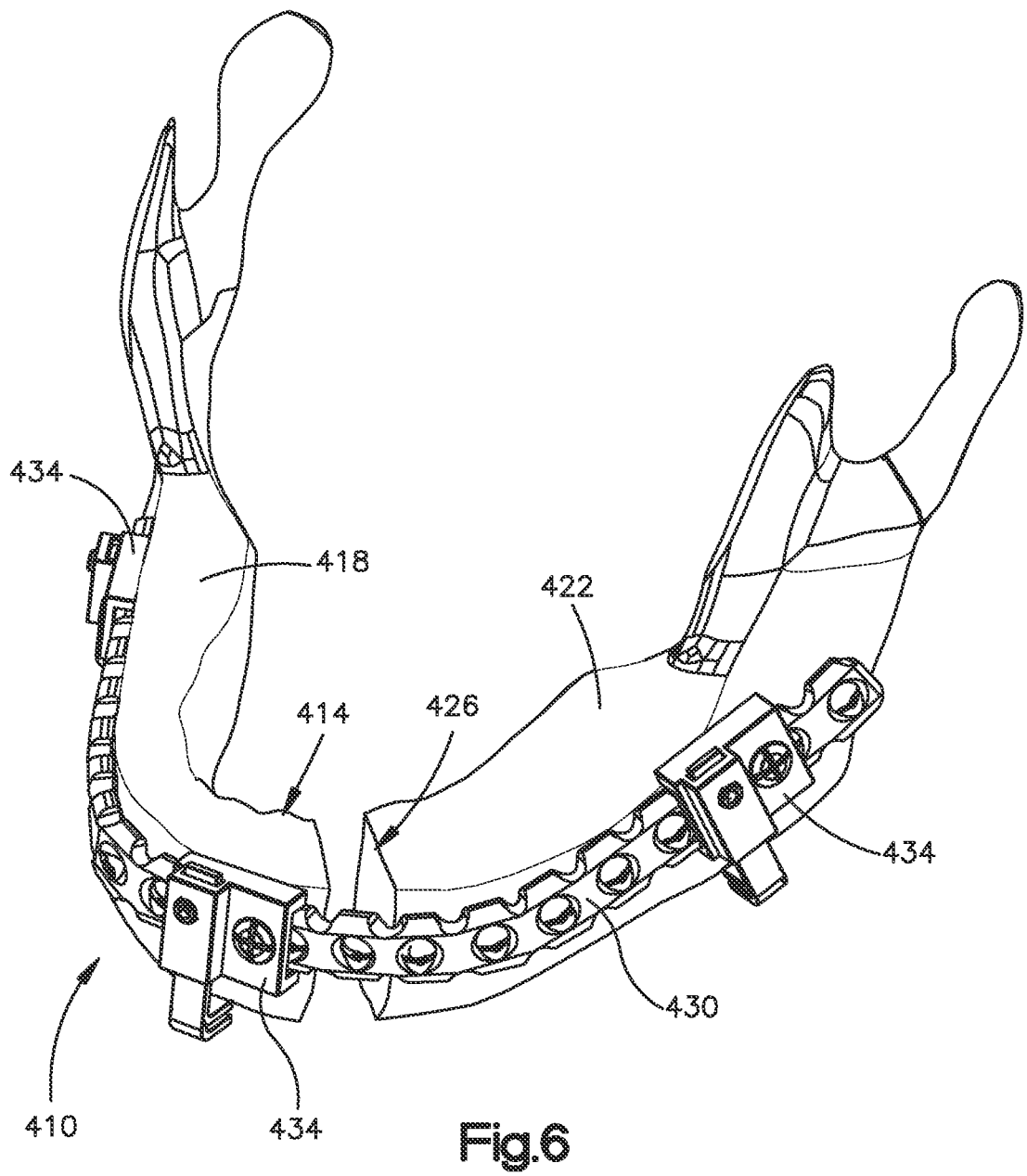
FIG. 6 is a perspective view of a bone fixation implant in accordance with another embodiment, the bone fixation implant configured to be affixed to a mandible that has been separated into a first part and a second part.

In another embodiment and in reference to FIG. 6 a bone fixation implant 410 is designed to be fixed to an underlying bone such as a mandible 414, for instance after the mandible 414 has been segmented into at least a first bone part 418 and a second bone part 422 that is separated from the first bone part 418 by a bone gap 426. For instance, the bone gap 426 can be created by a segmentation procedure, such as an osteotomy, or due to trauma, or a critical size defect for example. The bone fixation implant 410 is configured to attach to the first and second parts 418 and 422, and thereby fix the first and second parts 418 and 422 relative to each other so as to facilitate osteogenesis in the bone gap 426. The implant 410 is customized pre-operatively to reduce complications during surgery and time spent in the operating room by a patient. It should be understood that the implant 410 may affix more than two bone parts together.

As shown in FIGS. 7A-7E, the bone fixation implant 410 includes a longitudinal plate member 430 that is elongate and curved in the longitudinal direction L and a plurality of guides 434 that are coupled to the plate member 430. The longitudinal plate member 430 includes a bone engaging surface configured to abut the mandible, and an outer surface opposed to the bone engaging surface. As shown in FIG. 6, the bone fixation implant 410 connects and holds the first part 418 of the mandible and the second part 422 of the mandible relative to each other while osteogenesis occurs. The bone fixation implant 410 and components thereof, can be formed from a variety of biocompatible materials, such as cobalt chromium molybdenum (CoCrMo), titanium, and titanium alloys, stainless steel, ceramics, or polymers such as polyetheretherketone (PEEK), polyetherketoneketone (PEKK), and bioresorbable materials. A coating may be added or applied to the bone fixation implant 410 to improve physical or chemical properties or to provide medications. Examples of coatings include plasma-sprayed titanium coating or Hydroxyapatite.

Figure 7A:
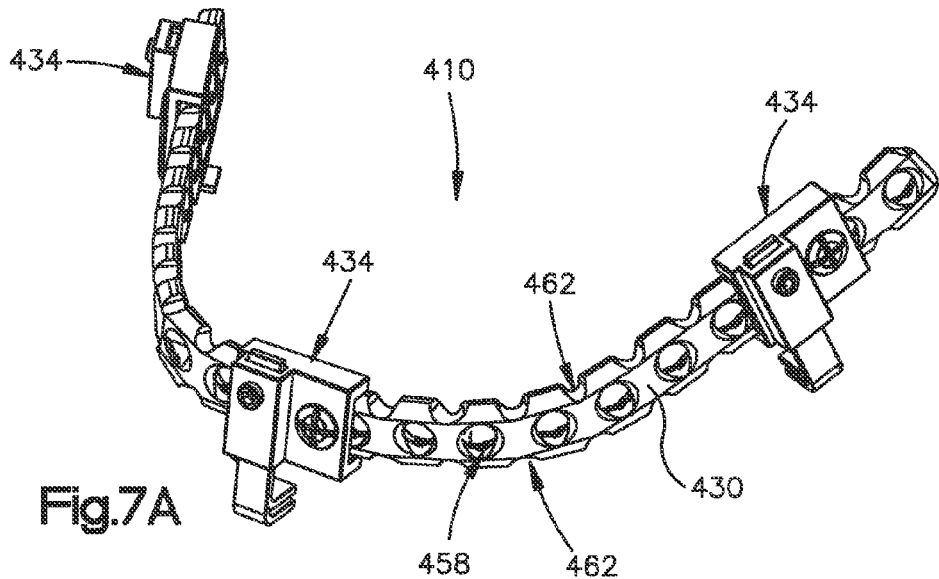
FIG. 7A is a perspective view of the bone fixation implant shown in FIG. 6, the bone fixation implant including a plate member and a plurality of guides coupled to the plate member.

As shown in FIGS. 6, and 7A-7E, the longitudinal plate member 430 is configured to wrap around the mandible 414 such that the plate member 430 spans across the gap 426 and can be attached to both the first part 418 and the second part 422 of the mandible 414. Therefore, as best shown in FIG. 7A, the longitudinal plate member 430 is curved such that it forms generally a C-shaped structure. Furthermore, the ends of the plate member 430 each angle up in the transverse direction T as they extend longitudinally. The curvature and shape of the longitudinal member 430 generally correspond to the shape of the mandible 414.

Additionally, the longitudinal member 430 includes a plurality of fixation element receiving apertures/holes 458 that extend from the outer surface of the longitudinal member 430 and through to the bone engaging surface. Each hole 458 is configured to receive a fixation element, such as a screw. Though it should be understood that any fixation element will suffice. The implant 410 is configured to be fastened to both the first part 418 and the second part 422 of the mandible 414 by inserting fixation elements through holes 458 of the longitudinal member 430 such that at least one fixation element engages the first part 418 of the mandible 414, and at least one fixation element engages the second part 422 of the mandible 414.

Figure 7B:
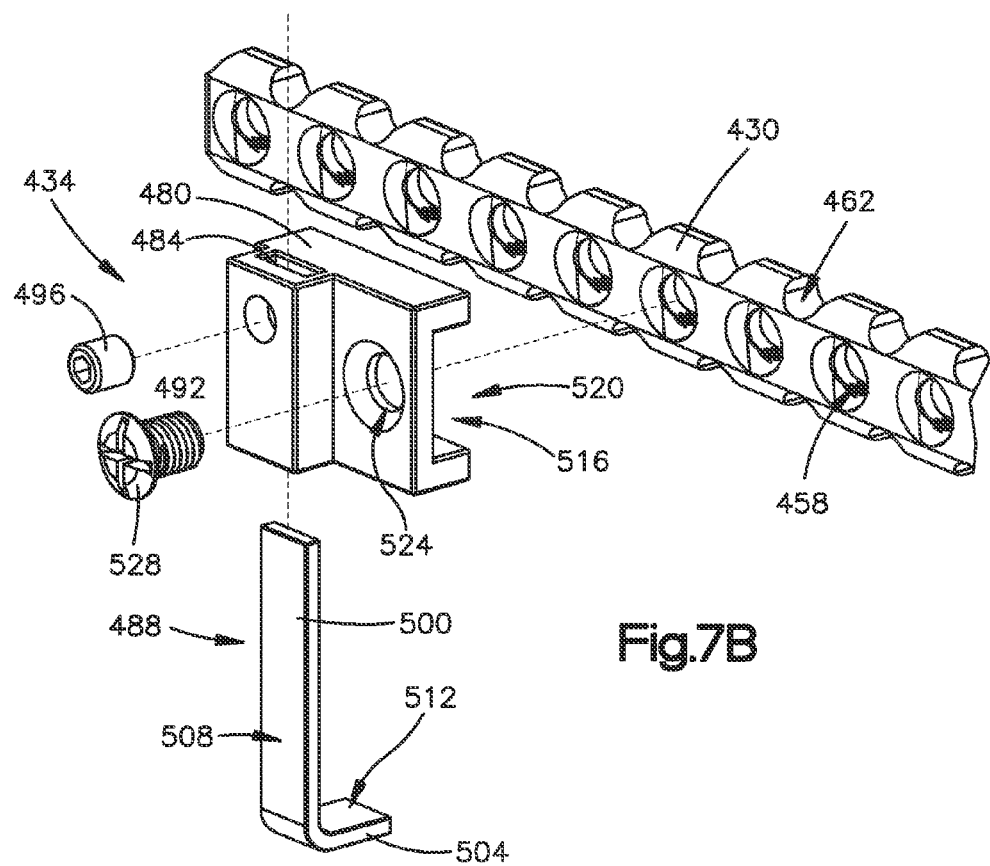
FIG. 7B is an exploded view of the guide shown in FIG. 7A, the guide including a guide body, a channel extending through the guide body and configured to receive the plate member, a transverse aperture extending transversely through the guide body, and a pusher translatable within the transverse aperture.

As shown in FIGS. 7A and 7B, the plate member 430 further defines a plurality of recesses or indents 462 along upper and lower sides of the plate member 430. The recesses 462 allow the plate member 430 to be pre-bent to conform to the shape of the mandible 414.

In particular, the longitudinal member 430, may be pre-bent to correspond to the post-operative shape of the first part 418 and the second part 422 of the mandible 414. In this regard the longitudinal member 430 is pre-bent prior to the segmentation procedure, so as to correspond to the general shape of the first and second parts of the mandible 414 after the segmentation procedure. While it is preferable that the member 430 is pre-bent such that no manual bending is required prior to placement of the implant 410 onto the mandible 414, the member 430 may be pre-bent such that only minimal bending is required prior to placement of the implant 410 onto the mandible 414 (e.g. bending that may take place when fastening the member 430 to the mandible 414). It should be understood, however, that the shape of the first part 418 and the second part 422 of the mandible 414 may be unchanged between the pre-operative and post-operative shape of the mandible 414. Therefore, the longitudinal member 430 may be pre-bent to correspond to both the pre-operative shape/position and the post-operative shape/position of the first part 418 and the second part 422 of the mandible 414.

As shown in FIG. 7A, the guides 434 of the implant 410 are spaced about the plate member 430 such that a guide 434 is coupled proximate to each end of the plate member 430 and a guide 434 is coupled to the plate member 430 proximate to the gap 426 that is defined between the first and second parts of the mandible 414. It should be understood that the guides 434 may be coupled anywhere along the plate member 430, as desired.

Figure 7E:
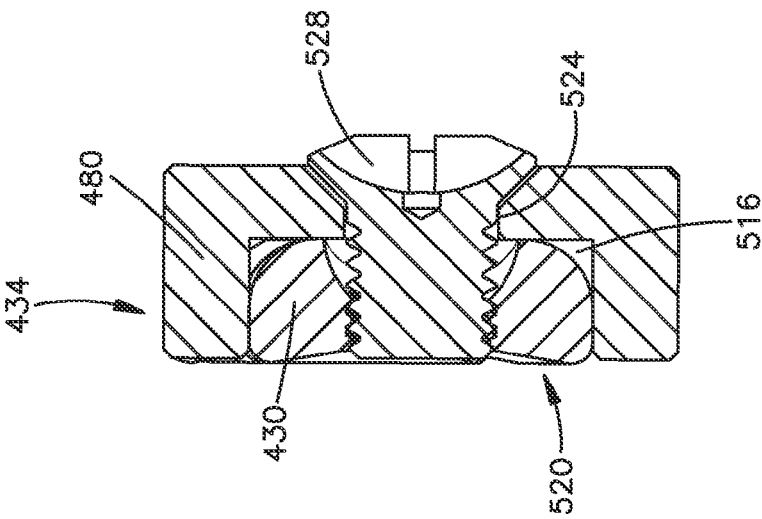
FIG. 7E is a sectional side elevation view of the guide shown in FIG. 7C through the line 7E-7E.
Figure 7D:
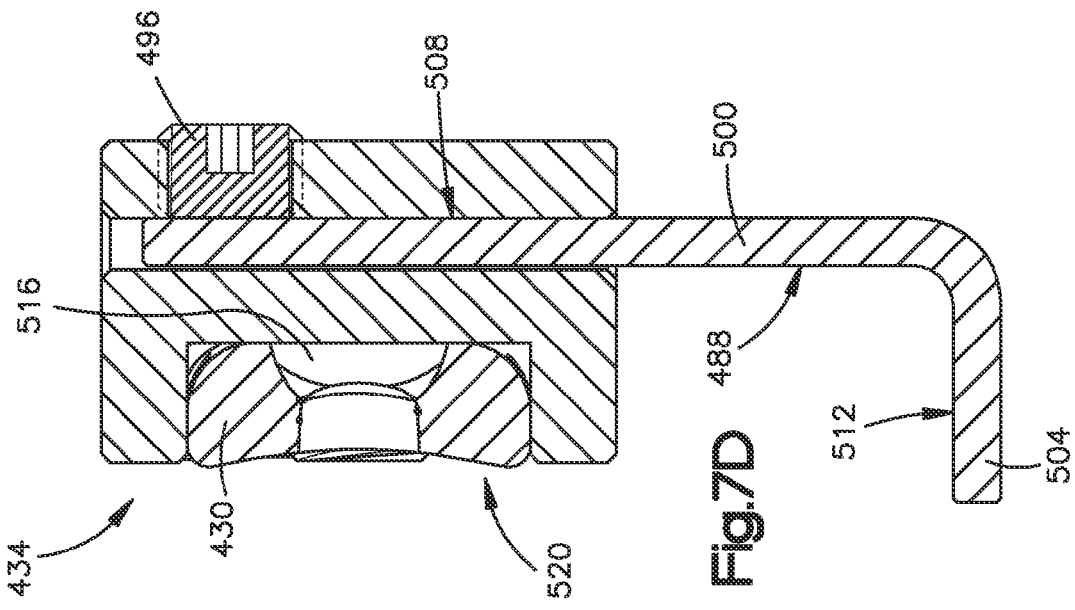
FIG. 7D is a sectional side elevation view of the guide shown in FIG. 7C through the line 7D-7D.
Figure 7C:
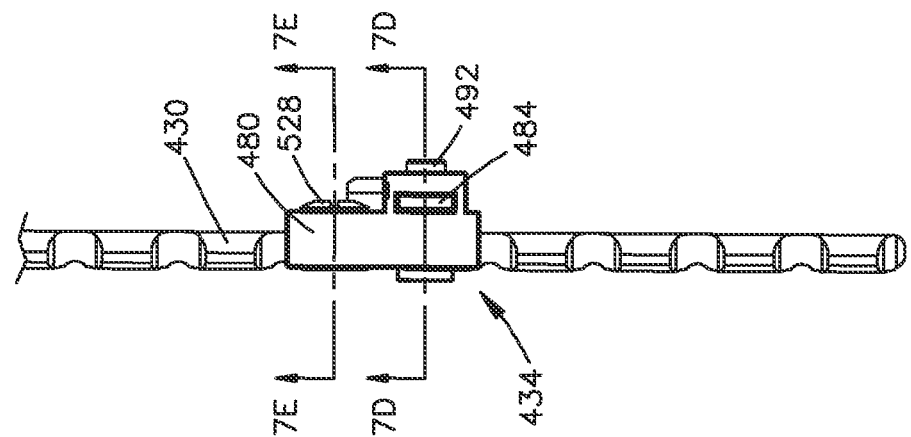
FIG. 7C is a partial top plan view of one of the guides coupled to the plate member.

As shown in FIGS. 7B-7E each guide 434 includes a guide body 480, a pusher aperture 484 that extends transversely through the body 480, and a pusher 488 that is translatable within the pusher aperture 484. As shown in FIG. 7C, the pusher aperture 484 is substantially rectangular shaped, though it should be understood that the transverse aperture 484 may have any desired shape so long as the pusher 488 can translate within the aperture 484. As shown in FIGS. 7B and 7D, the guide body 480 further includes a bore 492 that extends through a front face of the body 480 and into the pusher aperture 484. The bore 492 is configured to receive a set screw 496 that is configured to engage and lock the pusher 488 in place.

As shown in FIG. 7D, the pusher 488 includes a transverse portion 500 and a lateral portion 504 that extends from a bottom end of the transverse portion 500 toward the mandible 414. Therefore, the pusher 488 defines a substantially L-shaped structure. As shown, the transverse portion 500 is configured to be received by the pusher aperture 484 and is translatable within the pusher aperture 484. The transverse portion 500 is substantially flat and includes an outer contact surface 508 that is configured to be engaged by the set screw 496 when the pusher 488 is to be locked in place. The set screw 496 may be a plug that may be pushed against the pusher 488 or may include threads that engage threads defined by the bore 492. As shown in FIG. 7D, the lateral portion 504 is also substantially flat and includes an upper bone contacting surface 512 that is configured to abut a bottom of the mandible 414 when the implant 410 is properly positioned. When the pusher 488 is translated vertically up within the pusher aperture 484, the bone contacting surface 512 moves closer to the guide body 480. Therefore, the position of the implant 410 (or at least the plate member) is adjustable depending on position of the pusher 488 within the pusher aperture 484.

As shown in FIGS. 7D and 7E the guide 434 further includes a plate receiving channel 516 that extends longitudinally through the guide body 480. As shown in FIG. 7D, the channel 516 defines an opening 520 that allows the guide 434 to be placed over the front outer surface of the plate member 430. As shown in FIG. 7E, the guide 434 further includes a fixation receiving aperture 524 that extends through the body 480 and into the channel 516. The fixation receiving aperture 524 is configured to align with any one of the fixation receiving apertures 458 of the plate member 430. Therefore a fixation element 528 may be inserted through the aperture 524 of the guide 434 and into the aperture 458 of the plate member 430 to thereby affix the guide 434 to the plate member 430. The guide 434 may be permanently or temporarily affixed to the plate member 430.

The guides 434 are pre-operatively configured so as to align the plate member 430 with the mandible when the implant 410 is positioned against the mandible after the mandible has been separated so as toe define the bone gap. In this regard the pusher 488 may be pre-adjusted prior to the segmentation procedure, so that when the implant 410 is positioned against the mandible 414, the plate member 430 is properly aligned with the first part 418 and the second part 422 after the segmentation procedure. While it is preferable that the pusher 488 is pre-adjusted such that no additional adjustments are required prior to placement of the implant 410 onto the mandible 414, the pusher 488 may be pre-adjusted such that only minimal further adjustment is required prior to placement of the implant 410 onto the mandible 414. Because the pushers 434 are pre-adjusted, the implant 410 will fit correctly only at the desired location of the mandible 414 and provide a surgeon with positive assurance that they have achieved correct alignment and, therefore, a desired corrected shape.

Figure 8B:
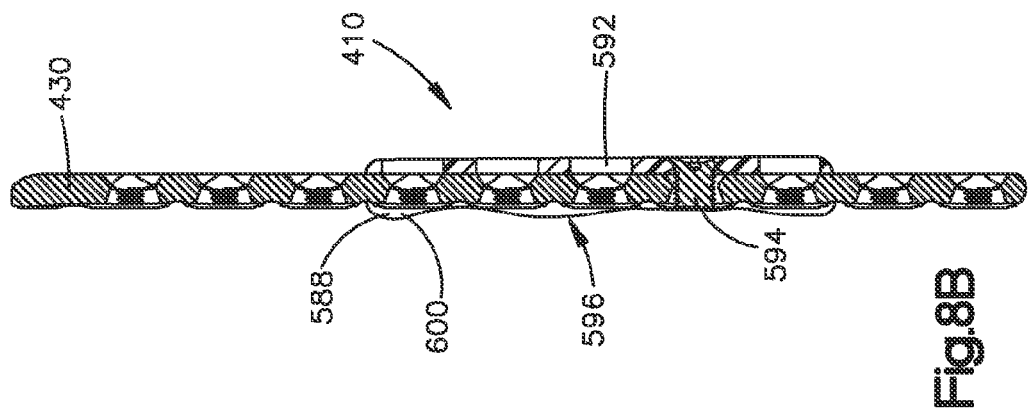
FIG. 8B is a sectional top plan view of the guide shown in FIG. 8A.
Figure 8A:
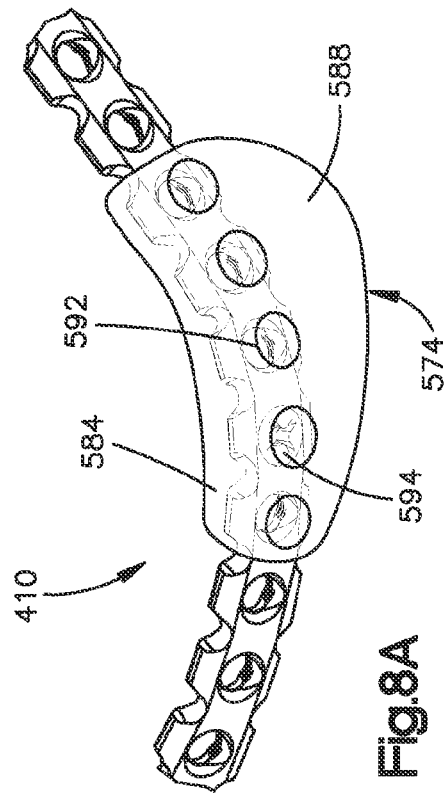
FIG. 8A is a perspective view of a guide constructed in accordance with another embodiment and for use with the implant shown in FIG. 6, the guide configured to be pre-shaped to correspond to a surface of the mandible.
Figure 8C:
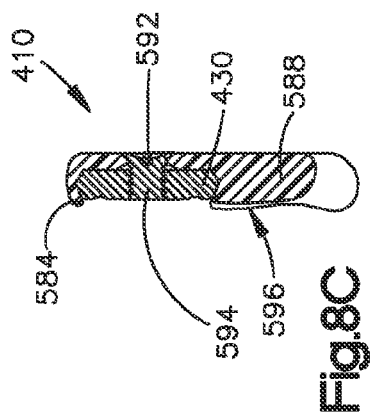
FIG. 8C is a sectional side elevation view of the guide show in FIG. 8A.

In another embodiment and in reference to FIGS. 8A and 8B, the bone fixation implant 410 may include a plurality of guides 574. As shown, each guide 574 includes a guide body 580 that is pre-configured or otherwise pre-shaped to correspond to the post-operative shape of the mandible 414. As shown, the guide body 580 is separated into at least a plate member fixation portion 584 and an alignment portion 588. As shown, the guide 574 further includes a fixation receiving aperture 592 that extends through the plate member fixation portion 584. The aperture 592 is configured to align with any one of the fixation apertures 458 of the plate member 430 such that a fixation element 594 may pass through the aperture 592 and into the aperture 458 to thereby couple the guide 574 to the plate member 430. The guide body 580 may be over-molded to be permanently attached to the plate member 430 or may be over-molded to correspond to the shape of the plate member 430 so that when the guide 580 is attached to the plate member 430, the fixation portion 584 will lie flush against the plate member 430.

As shown in FIGS. 8A and 8B, the alignment portion 588 extends from the fixation portion 584 such that the alignment portion 588 is configured to abut an outer surface of the mandible 414. As shown in FIG. 8B, the alignment portion 588 defines an inner bone contacting surface 596 that is pre-operatively shaped to correspond to the post-operative shape of the mandible 414. That is, each guide body 580 is pre-operatively shaped to correspond to a specific portion of the mandible so as to align the plate member 430 with the mandible when the implant is positioned against the mandible after the mandible has been separated.

In this regard the guide bodies 580 are pre-shaped prior to the segmentation procedure, so as to correspond to an outer surface of a portion of the mandible 414 after the segmentation procedure. While it is preferable that the guide bodies 580 are pre-shaped such that no manual bending is required prior to placement of the implant 410 onto the mandible 414, the guide bodies 580 may be pre-shaped such that only minimal bending is required prior to placement of the implant 410 onto the mandible 414. Therefore, alignment portion 588 or at least the bone contacting surface 596 of the alignment portion 588 defines several non-linear undulations 600 that correspond to particular surface portions of the mandible 414. Because the guide bodies 580 are pre-shaped, they will fit correctly only at the desired location of the mandible 414 and provide a surgeon with positive assurance that they have achieved correct alignment of the implant.

Similar to the bone implant 10, the bone implant 410 is manufactured and configured pre-operatively. Prior to the orthognathic surgery being performed, a 3-D image of the patient's skull, and in particular the patient's mandible, such as mandible 414 is obtained. This may be completed with a CT scanning device (such as device 200 shown in FIG. 4) or the like, with slices smaller than 1 mm preferred, and optimally between 0.2-1 mm. A high resolution for the slices is preferred, since the exact shape of the mandible 414 should be determined from the CT scan slices. It will be appreciated that other scanning devices 200 besides a CT scanning device may be used so long as they provide three dimensional data corresponding to the shape of the mandible 414.

Once the 3-D image of the patient's skull/mandible is obtained, the image is loaded into a computer (such as computer 204 shown in FIG. 4) to create a virtual model of the skull for manipulation by a user such as the surgeon. The computer 204 may be local (same general area as the CT scanning device 200) or remote where the image must be sent via a network. Similarly, the image loaded onto the computer 204 may be manipulated by a user that is working locally or remotely. Typically, however, the image is manipulated remotely by the surgeon who will be performing the orthognathic surgery.

The virtual model of the skull may be manipulated by the surgeon using standard software typical in the art. For example, Mimics, a software commercially available from Materialise, having a place of business in Leuven Belgium, may be used to process and manipulate the virtual model obtained from the CT scanning device 200. The software allows the surgeon to analyze the patient's mandible and pre-operatively plan the patient's orthognathic surgery including the shape and/or configuration of the bone fixation implant 414.

Using the 3-D model the surgeon or other operator may manipulate the mandible 414 by (i) cutting the mandible 414 to form the gap 426, (ii) repositioning the first part 418 of the mandible 414 from a first undesired position to a second desired position, and/or (iii) repositioning the second part 422 of the mandible 414 from a first undesired position to a second desired position. Once the first part 418 and/or the second part 422 are positioned and the virtual model portrays the post-operative shape and position of the patient's mandible, as approved by the surgeon, a virtual model of a bone fixation implant, such as the bone fixation implant 410 shown in FIGS. 7A-7E or 8A and 8B, can be made. At this point, it should be understood that the virtual model of the skull and in particular the mandible has a post-operative shape and position. Therefore, the longitudinal plate member 430 and the guides 434 or 474 of the bone fixation implant 410 that is being made will correspond to the post-operative shape/position of the patient's mandible.

For bone fixation implants 410 that include a guide 434, the virtual model of the bone fixation implant 410 may be downloaded and the pusher 488 of the guide 434 may be pre-configured or otherwise pre-adjusted to match that of the model. For bone fixation implants 410 that include a guide body 574, the virtual model of the implant 410 is transferred from the computer 204 to a CAD/CAM milling/manufacturing machine (such as machine 220 shown in FIG. 4) or the like. The manufacturing machine 220 will machine the guide 574 out of any desired material to conform to the post-operative shape of the mandible 414. Once the guide 434 has been adjusted, or the guide 574 has been milled, the surgeon may begin the orthognathic surgery on the patient.

Figure 9C:
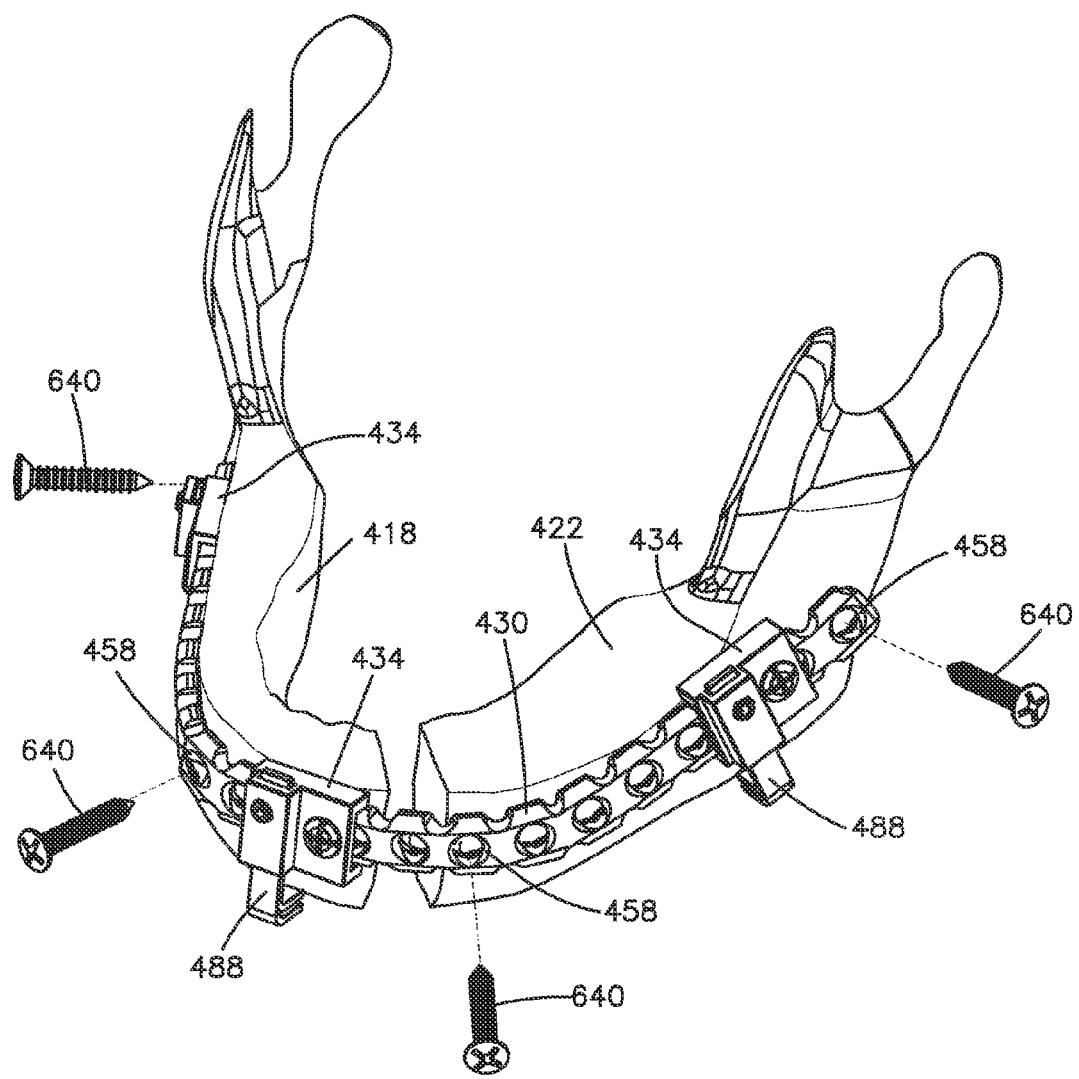
FIG. 9C is a perspective view of the bone fixation implant of FIGS. 7A-7E being attached to the first and second parts of the mandible.

FIGS. 9A-9E show an example method of performing an orthognathic surgery using the bone fixation implant 410. It should be understood that prior to the surgery, the bone fixation implant 410 is pre-configured to substantially correspond to the individual patient's mandible. FIG. 9A shows an example mandible 414 that needs to be repositioned. As shown, the mandible 414 at this point has a pre-operative shape. An osteotomy is to be performed on the mandible 414 to thereby separate the mandible 414 into a first part 418 and a second part 422 as shown n FIG. 9B.

Once the osteotomy is performed and the gap 426 is made, if needed, the first part 418 and/or the second part 422 of the mandible 414 may be repositioned to the post-operative shape. The bone fixation implant 410 may then be placed onto the mandible 414. As stated before, the bone fixation implant 410 is pre-configured to correspond to the post-operative shape of the mandible 414, and therefore will be properly aligned when set in place. As shown in FIG. 9C, for embodiments that include guides 434, the upper bone contacting surfaces 512 of the pushers 488 will each abut the bottom surface of the mandible 414 once the implant 410 is properly positioned.

Alternatively, for embodiments that include guides 574, the alignment portions 588 of the guides 574 will lie flush against the mandible 414 when the implant 410 is properly positioned.

Figure 9D:
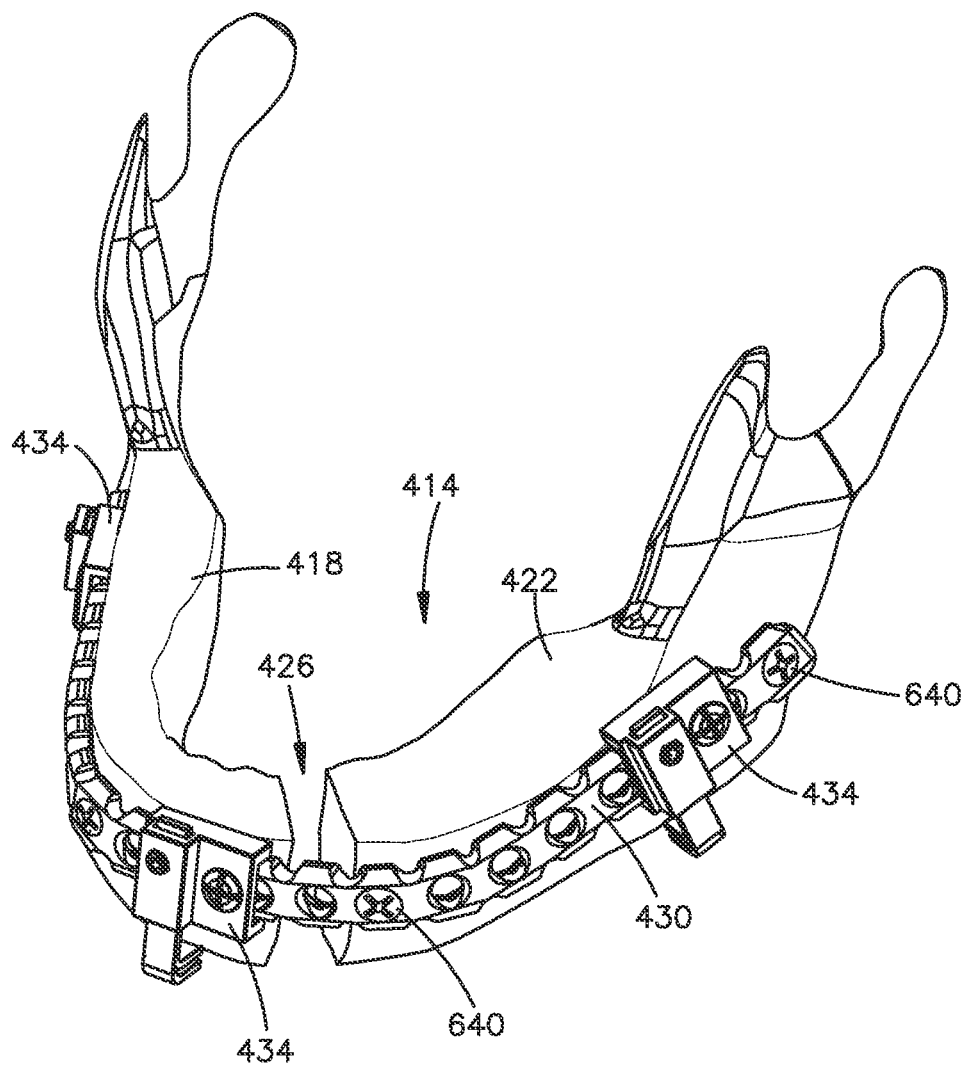
FIG. 9D is a perspective view of the bone fixation implant fully attached to the first and second parts of the mandible.

As shown in FIGS. 9C and 9D, once properly positioned, a plurality of screws 640 may be inserted into the fixation apertures 458 of the plate member 430. As shown, the plate member 430 is affixed to both the first part 418 and the second part 422 of the mandible 414. Therefore, the bone fixation implant 410 is affixed to the mandible 414 on either side of the gap 426.

Figure 9E:
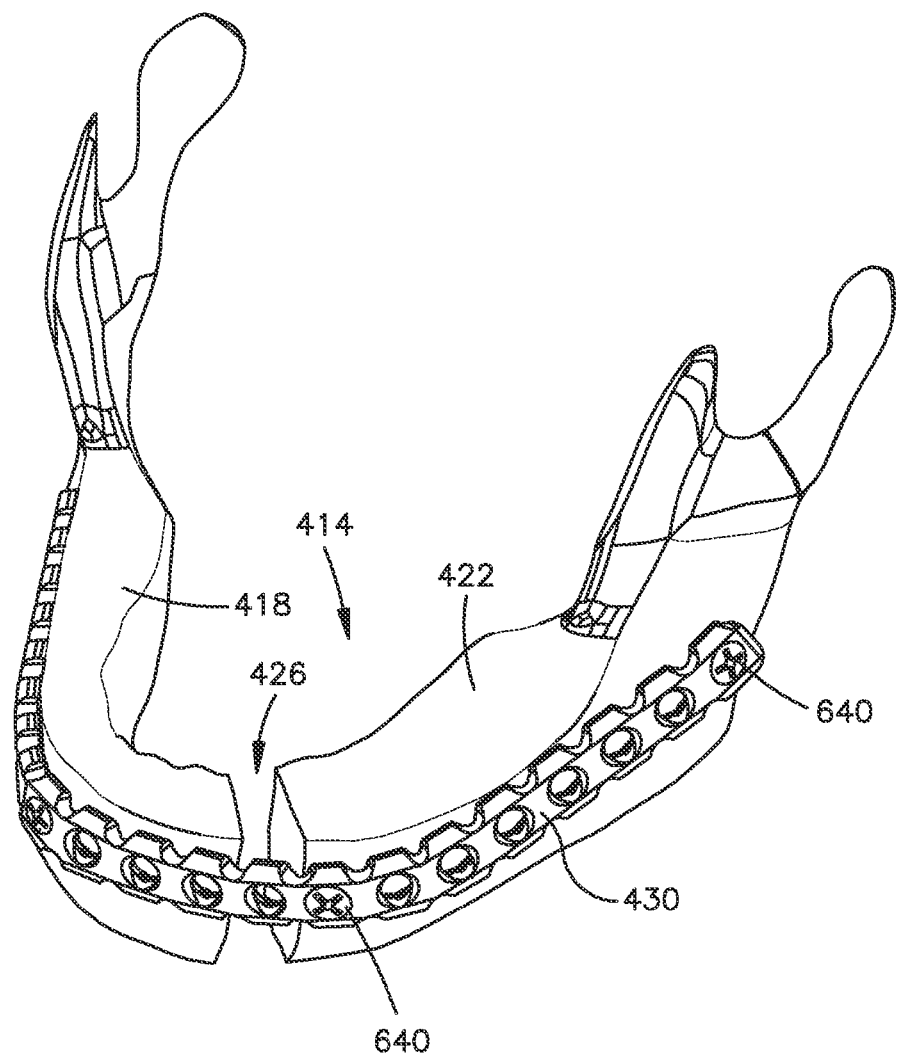
FIG. 9E is a perspective view of the bone fixation implant fully attached to the first and second parts of the mandible with the guides removed.

As shown in FIG. 9E, the guides 434 (or guides 574) may then be removed from the bone fixation implant 410 thereby leaving the plate member 430 affixed to the mandible 414. Therefore, the surgery may be completed, and the implant 10 may either remain within in the patient or be removed at a later time.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description. For example, while the bone fixation implant 10 is shown as having a removable bridge member 42, it should be understood that the bone fixation implant may remain intact after it has been installed. In other words, the longitudinal member 30 of the bone fixation implant 10 may be a single continuous plate that is configured to remain a single piece after installation of the bone plate 10. Furthermore, while the holes 180 of the osteotomy guiding implant 110 are positioned in the fingers 134 of the implant 110 such that a guide path is created for the osteotomy to be performed along the holes, the holes 180 may be positioned to create an alternative guide. For example, the holes 180 may be positioned to create holes in the maxilla 14 that line up with the holes 58 defined by the longitudinal member 30 of the bone fixation implant 10. In such a case the osteotomy would be performed above the holes 180. Furthermore, while the bone fixation implant 10 and the osteotomy guiding implant 110 have been described for use in orthognathic surgeries involving the maxilla, and the bone fixation implant 410 has been described for use in orthognathic surgeries involving the mandible should be understood that the bone fixation implant 10 and the osteotomy guiding implant 110 may be used in orthognathic surgeries involving the mandible, and the bone fixation implant 410 may be used in orthognathic surgeries involving the maxilla. Additionally, the bone fixation implant 10, the osteotomy guiding implant 110, the bone fixation implant 410 and the described concepts are not limited to orthognathic surgeries and may be utilized in surgeries for other parts of the body that may need to affix a first segmented portion of bone relative to a second integral portion of bone.

What is claimed:

1. A method of customizing a pre-shaped implant configured to fix at least a first mandibular bone part relative to a second mandibular bone part that is separated from the first mandibular bone part by a bone gap, the method comprising:
    obtaining a pre-operative 3-D model of a patient's mandible in a computer, so as to define a first modeled part of the mandible and a second modeled part of the mandible that define a first position relative to each other;
    manipulating the pre-operative 3-D model of the mandible into a planned post-operative shape whereby the first modeled part of the mandible and the second modeled part of the mandible define a second position relative to each other; and custom constructing a bone fixation implant to match the planned post-operative shape of the mandible such that the bone fixation implant is configured to attach to the first and second mandibular bone parts when the first and second mandibular bone parts define the second position relative to each other, the implant including a plate member and at least one guide coupled to the plate member, the custom constructing step comprising:

prior to segmenting the second mandibular bone part from the first mandibular bone part, bending the plate member so as to attach to the first and second mandibular bone parts after the second mandibular bone part has been segmented from the first mandibular bone part; and prior to segmenting the second mandibular bone part from the first mandibular bone part, configuring the at least one guide to align the plate member with the mandible when the implant is positioned against the mandible after the second mandibular bone part has been separated from the first mandibular bone part.

2. The method of claim 1, wherein the at least one guide includes a guide body and the configuring step comprises pre-shaping the guide body to correspond to the post-operative shape of the mandible so as to align the plate member with the mandible when the implant is positioned against the mandible after the mandible has been separated.

3. The method of claim 2, further comprising over molding the guide body onto the plate member.

4. The method of claim 2, wherein the guide body is made from a biocompatible material.

5. The method of claim 1, wherein the at least one guide includes a guide body, a pusher aperture that extends transversely through the guide body, and a pusher that is disposed within the pusher aperture, the configuring step comprising positioning the pusher pre-operatively so as to abut a bottom of the mandible when the implant is positioned against the mandible after the mandible has been separated.

6. The method of claim 5, the configuring step further comprising pre-operatively adjusting the pusher within the transverse aperture.

7. The method of claim 1, wherein the second position is different than the first position.

8. The method of claim 1, wherein the first position is the same as the second position.

* * * * *